(12) United States Patent
Caviglioli et al.

(10) Patent No.: US 9,078,825 B2
(45) Date of Patent: Jul. 14, 2015

(54) METHOD FOR THE PRODUCTION OF BIOADHESIVE COMPACT MATRICES

(75) Inventors: Gabriele Caviglioli, Genoa (IT); Brunella Parodi, Genoa (IT); Eleonora Russo, Genoa (IT); Sergio Cafaggi, Genoa (IT); Gaetano Bignardi, Genoa (IT); Paola Cirrincione, Genoa (IT)

(73) Assignee: Università degli Studi di Genova (IT)

( * ) Notice: Subject to any disclaimer, the term of this patent is extended or adjusted under 35 U.S.C. 154(b) by 243 days.

(21) Appl. No.: 13/063,146

(22) PCT Filed: Sep. 10, 2009

(86) PCT No.: PCT/EP2009/006567
§ 371 (c)(1),
(2), (4) Date: Apr. 29, 2011

(87) PCT Pub. No.: WO2010/028826
PCT Pub. Date: Mar. 18, 2010

(65) Prior Publication Data
US 2012/0122845 A1    May 17, 2012

(30) Foreign Application Priority Data
Sep. 12, 2008  (EP) ..................................... 08425600

(51) Int. Cl.
| | | |
|---|---|---|
| A61K 47/38 | (2006.01) | |
| A61K 31/554 | (2006.01) | |
| A61K 47/32 | (2006.01) | |
| A01N 43/00 | (2006.01) | |
| A61K 31/00 | (2006.01) | |
| C08L 1/26 | (2006.01) | |
| C09K 3/10 | (2006.01) | |
| C08B 11/193 | (2006.01) | |
| D06P 1/44 | (2006.01) | |
| C08K 5/1545 | (2006.01) | |
| C09D 133/02 | (2006.01) | |
| A61K 9/20 | (2006.01) | |
| A61K 31/55 | (2006.01) | |
| A61K 31/64 | (2006.01) | |

(52) U.S. Cl.
CPC ............ *A61K 9/2018* (2013.01); *A61K 9/2027* (2013.01); *A61K 9/2054* (2013.01); *A61K 31/55* (2013.01); *A61K 31/64* (2013.01)

(58) Field of Classification Search
None
See application file for complete search history.

(56) References Cited

U.S. PATENT DOCUMENTS

| | | | |
|---|---|---|---|
| 5,707,655 A | 1/1998 | Kanikanti et al. | |
| 6,303,147 B1 * | 10/2001 | Gilis | 424/484 |
| 6,509,036 B2 * | 1/2003 | Pather et al. | 424/466 |
| 2005/0013857 A1 * | 1/2005 | Fu et al. | 424/464 |
| 2006/0099245 A1 * | 5/2006 | Kumar et al. | 424/451 |
| 2007/0219175 A1 | 9/2007 | Jain et al. | |
| 2009/0281070 A1 | 11/2009 | Kaltsatos et al. | |

FOREIGN PATENT DOCUMENTS

WO    01/95888 A1    12/2001

OTHER PUBLICATIONS

Miyazaki et al (2000). "Oral mucosal bioadhesive tablets of pectin and HPMC: in vitro and invo evaluation". International Journal of Pharmaceutics, 204: 127-132.*
Hart, John Seely. A Manual of composition and rhetoric, 1871, p. 50.*
Lubrizol ("Lubrizol-1")—"Polymers for Pharmaceutical Application." Retrieved on Sep. 8, 2014. Retrieved from the internet <URL: http://www.lubrizol.com/Life-Science/Documents/Pharmaceutical/Bulletins/Bulletin-01---Polymers-for-Pharmaceutical-Applications.pdf>.*
Lubrizol ("Lubrizol-2")—"Toxicity of Carbopol Polymers as a Class." Retrieved on Sep. 8, 2014. Retrieved from the internet <URL: http://www.lubrizol.com/Personal-Care/Documents/Technical-Data-Sheets/TDS-093-Toxicity-Carbopol%C2%AE-As-A-Class.pdf>.*

* cited by examiner

*Primary Examiner* — Anoop Singh
*Assistant Examiner* — Doan Phan
(74) *Attorney, Agent, or Firm* — Akerman LLP

(57) ABSTRACT

A method for the preparation of a bioadhesive compact matrix, which comprises the preparation of a uniform mixture of powders comprising one alkylcellulose or one hydroxy alkylcellulose and a non-water-soluble, water-swellable crosslinked polycarboxylic polymer; the preparation of compressed units starting from such powder mixture by direct compression and finally the heating of the compressed units thus obtained to a temperature in the range of 80-250° C. for a time of 1-60 minutes; the powder mixture can also comprise at least one active substance and the compressed units thus obtained are characterized by a prolonged release, and have a release kinetics of the active substance substantially of zero order in an aqueous solution at pH 4-8.

16 Claims, 22 Drawing Sheets

METHOD FOR THE PRODUCTION OF BIOADHESIVE COMPACT MATRICES

CROSS-REFERENCE TO RELATED APPLICATIONS

This application is a §371 national stage of PCT/EP2009/006567, filed Sep. 10, 2009, which claims priority to European Patent Application No. 08425600.7, filed Sep. 12, 2008, the entirety of which are hereby incorporated by reference.

FIELD OF APPLICATION

The present invention regards the chemical industry field in general, and in particular the pharmaceutical industry field.

In particular, the invention refers to a method for the production of compact matrices, which can be tablets or devices that can be used for the release of active substances, characterised by a prolonged release, and the compact matrices thus obtained. More in particular, the invention relates to a method for the preparation of compact matrices, which can constitute tablets or devices for the release of active substances, which provide for a step of direct compression of specific components and a step of heat treatment.

PRIOR ART

For about 40 years, pharmaceutical research has studied and developed new systems for modifying and controlling the release of active substances to living organisms.

The modifications tend to prolong the release (extended or prolonged release) of the drugs into the organism, in order to reduce the frequency of administration and possibly control the release rate of the active substances (controlled release, CR), seeking to obtain release kinetics of zero order, i.e. independent of the drug dose loaded in the dosage form (Extended Release and Targeted Drug Delivery System, in Remington The Science and Practice of Pharmacy 21$^{st}$ Edition, chapter 47 pages 939-936).

Other modifications are aimed at making the release of the drug occur in a specific zone of the organism, as a function of specific stimuli (pH, temperature, enzyme activities, ionic strength) (Morishita M. et al. J Drug Deliv Sci Technol 16(1): 19-24, 2006) or after a certain time period or with pre-established time intervals (delayed or pulsatile release) Gazzaniga et al. European Journal of Pharmaceutics and Biopharmaceutics 68(1):11-18, 2008).

In particular, in the oral administration forms, the prolonged release of a drug can be obtained through the use of suitable polymers, used in small quantities as coating film or in greater quantities in order to form matrix systems. In both cases, the composition of the film or matrix is capable of influencing the release of the active substances, and in many cases the release rate can thus be designed beforehand and verified through appropriate "in vitro" dissolution studies (Kanjickal D G, Lopina S T. Modeling of drug release from polymeric delivery systems—A review. Critical Reviews in Therapeutic Drug Carrier Systems 21(5):345-386), 2004).

The films can be employed directly in the coating of tablets or in the coating of granules or pellets that can be administrated either as such or upon encapsulation or conversion into tablets.

The polymers used for forming the matrices control the release of the drugs through their different dissolution or erosion rates, or through the diffusion of the active substance in the matrix, which in the case of hydrophilic polymers can swell and gel and be more or less easily eroded (Brazel C S, Peppas N A. Mechanisms of solute and drug transport in relaxing, swellable, hydrophilic glassy polymers. Polymer 40(12):3383-3398, 1999).

There are more "engineered" systems called drug delivery systems (DDS) or devices obtainable through costlier and more complex industrial processes (Hilt J Z, Peppas N A, International Journal of Pharmaceutics 306(1-2):15-23, 2005). The DDS prototype are the so-called "osmotic" systems which utilise semi-permeable membranes and the osmotic pressure generated inside these membranes for prolonging the release of the drug. The release of the drug in solution or in suspension occurs through the micro-holes produced by means of a laser ray on the surface of the tablet, at constant rate according to a release kinetics of zero order (U.S. Pat. No. 4,160,020; WO 03/075894 A1). Such systems can lead to the drawback of the massive release of the entire loaded dose, phenomenon known as "dumping dose", with related toxic effects for the organism, linked to the type of active substance transported. From this standpoint, the "pelletised" forms offer more guarantees, also in the quality control step of the industrial production.

The matrix systems utilise non-water-dispersable or hydrophobic systems like ethylcellulose or hydrophilic polymers capable of swelling in the presence of aqueous fluids such as, for example, hydroxypropylmethylcellulose, which as a function of its molecular weight and degree of substitution can also form gels that are not very erodible.

These matrix systems generally are produced through a granulation or "pelletisation" process, both for obtaining an improved homogenisation of the components and to avoid the segregation phenomena in the powders mixture and during their compression, and to make possible the formation of a matrix which effectively controls the release of the drug. Such processes can be developed in wet conditions (wet granulation, spray drying) or dry conditions (dry granulation or roller compaction and hot melt extrusion) (Oral Solid Dosage Forms, in Remington The Science and Practice of Pharmacy 21.sup.ST edition, chapter 45 pages 889-928).

Naturally, the industrial processes which involve a granulation step are considered anti-economical, and thus the industries tend to employ direct compression processes, also thanks to the excipients developed and placed on the market for this purpose (Gohel M C, Jogani P D. Journal of Pharmacy and Pharmaceutical Sciences 8(1):76-93, 2005; Goto K, et al. Drug Development and Industrial Pharmacy 25(8)869-878, 1999; Michoel A, et al. Pharmaceutical Development and Technology 7(1)79-87, 2002).

Most of the CR systems on the market (Colombo et al. Swelling matrices for controlled drug delivery: gel-layer behaviour, mechanisms and optimal performance. Pharm Sci Technol Today 3(6), 2000) control the release of the drugs through matrices based on the use of hydrophilic polymers (Peppas N A et at Hydrogels in pharmaceutical formulations. European Journal of Pharmaceutics and Biopharmaceutics 50(1)27-46, 2000).

As said, generally the systems which effectively control the release of active substances through a polymer matrix are obtained through a process of wet granulation (EP 1 681 051A1; U.S. Pat. No. 5,549,913).

In fact, there are not many examples of controlled release through polymer matrices obtained by direct compression. For example, M. E. Pina and colleagues reported (Pharmaceutical Development and Technology 11(2):213-228, 2006) a modified release for Ibuprofen, a drug which is not very soluble in water, through a matrix, obtained via direct compression, mainly composed of the hydrophilic polymer swelling in aqueous medium hydroxypropylmethylcellulose (HPMC) medium. Peppas and Siepmann (Advanced Drug Delivery Reviews 48(2-3):139-157, 2001) have fully reviewed the modelling of the drug release from matrices composed of HPMC.

E Crowley and colleagues (International Journal of Pharmaceutics 269(2):509-522, 2004) report a modified release for Guaifenesin, water-soluble drug, through a matrix, obtained via direct compression, made of the hydrophobic polymer ethyl cellulose.

The processes for obtaining matrices for CR that involve heat treatments deserve a particular mention, especially the emerging technology of the extrusion of thermoplastic polymers known as Hot Melt Extrusion (HME), which generates monolithic matrices that can be utilised for obtaining granulates or, directly, regular geometric forms usable as "tablets".

This method involves the melting of the polymer, in the presence of possible process adjuvants, by means of a heating to a temperature 10-60° C. higher than the glass transition (Tg) of the amorphous polymers or the melting temperature of the semi-crystalline polymers. Such a melt, after having acquired a suitable viscosity, is forced to flow through a slit of regular section, thus assuming the form of such section for subsequent cooling (Repka M A, et al. Drug Development and Industry Pharmacy Part 133(9):909-926 and Part II 33(10):1043-1057, 2007).

It has been found in the prior art that in some cases, it is possible to influence the release of active substances from tablets by directly subjecting the tablets to a heat treatment step.

Omelczuck et al (Pharmaceutical Research 10, 542-548, 1993) reported that the heat treatment (between 40 and 80° C. for 24 h) of tablets containing poly(dl-lactic acid) (PLA) and microcrystalline cellulose prolonged the release of theophylline. From the reported dissolution curves, it is inferred that such release occurs by following complex kinetics, different from the zero order kinetics.

Azarmi S. et al (International Journal of Pharmaceutics 246 (2002), 171-177) verified that indomethacin tablets, prepared via direct compression of the drug with Eudragit RS PO or RL PO and lactose in a 3:3:4 ratio and subjected to heating at a temperature higher than 50 or 60° C. for a time of 2-24 hours, had a prolonged release with respect to tablets that were not subjected to heat treatment, without appreciable modification of the tensile strength.

Similar results were obtained, still by Azarmi et al. (Pharmaceutical Development and Technology, 10: 233-239, 2005) with diclofenac sodium tablets (obtained via direct compression of diclofenac sodium, Eudragit RS PO or RL PO and lactose 3:4:3), subjected to heating at 50-70° C. for 2-24 hours.

Previously, Lila et al. (Drug Development and Industrial Pharmacy, 24(1), 45-50, 1998) had investigated the effect of a heat treatment at 60° C. on tablets of diclofenac sodium/Eudragit NE40D/microcrystalline cellulose, and had noted the achievement of a prolonged release associated with an increase of the tablet tensile strength.

The observations on the effects of tablet heat treatment on the drug release properties appear limited to the above examples, i.e. to tablets based on Eudragit or containing PLA, and the results obtained, following long heating times, are rather limited with regard to both the prolonging of the release time and the obtained release kinetics.

In the controlled release field, the use is also known of non-water-soluble cross-linked polymers, which are however hydrophilic and swellable in aqueous medium (Brazel C S, Peppas N A 1999. Mechanisms of solute and drug transport in relaxing, swellable, hydrophilic glassy polymers. Polymer 40(12):3383-3398). Belonging to this category is Polycarbophil (CAS RN 9003-01-4) (Handbook of Pharmaceutical Excipients, Fifth edition, Pharmaceutical Press, p. 539-541, 2006), a polymer of polyacrylic acid cross-linked with divinyl glycol, which is known for being used in the production of CR pharmaceutical forms, for example in the form of tablets, disks or films provided with bioadhesive properties. As an example, one can see the patent applications WO 2005/065685 and WO 01/95888 and U.S. Pat. No. 5,102,666.

Polycarbophil is used inside the pharmaceutical forms, above all for its bioadhesive properties. Robinson et al. (Journal of Pharmaceutical Sciences 89(7):850-866, 2000) have reviewed the bioadhesive properties of Polycarbophil and other polymers used in the drug forms. Repka et al. (Journal of Controlled Release 70(3):341-351, 2001) have studied the bioadhesive properties of buccal films obtained via HME also containing Polycarbophil.

Worthy of note is also the pH-dependent ability of Polycarbophil to swell, absorbing water up to 1000 times its original volume and 10 times its original diameter. According to the prescriptions of the monograph of the US Pharmacopeia 31 related to Polycarbophil, the absorbing power, towards a sodium bicarbonate solution, must not be less than 62 g per 1 g of dry polymer. For these characteristics, the Polycarbophil is employed not only in pharmaceutical preparations, but also in food supplements for the treatment of intestinal malfunctions, chronic constipation, diverticulitis and the irritable bowel syndrome.

WO 01/95888 A1 discloses bioadhesive sustained release tablets comprising an active ingredient that is metabolized by 5α-reductase, a water soluble polymer, such as e.g. hydroxypropylmethylcellulose, and a water insoluble, water-swellable cross-linked polycarboxylic polymer, in particular polycarbophil. The method for preparing such tablets does not comprise any heating step. WO 2005/065685 discloses bioadhesive sustained release tablets comprising an active ingredient and a polymer system comprising at least two polymers, wherein one is an acid insoluble polymer and the other is a bioadhesive polymer; the polymer system may include for instance ethylcellulose, polycarbophil and microcrystalline cellulose. No heating steps are envisaged in the manufacturing process for the tablets according to this document.

SUMMARY OF THE INVENTION

In a first aspect thereof, the present invention has the object of providing a compact matrix containing a cross-linked polycarboxylic polymer, non-erodible and provided with bioadhesivity, capable of swelling by water absorption, forming a non-erodible gel layer usable i.a. for the prolonged release of active substances. Such an object is attained by means of a method for the preparation of a compact bioadhesive matrix, which comprises the following steps:

preparing a uniform mixture of powders comprising at least one alkylcellulose or one hydroxyalkylcellulose and a non-water-soluble, water-swellable, cross-linked, polycarboxylic polymer;

preparing compressed or compacted units starting from said powder mixture by direct compression or dry compaction;

subjecting the compressed or compacted units thus obtained to heating at a temperature in the range of 80-250° C. for a time in the range of 1-60 minutes.

In another aspect thereof, the invention has the object of providing a compressed unit, comprising the aforesaid compact, bioadhesive matrix, capable of swelling in water, for the release of active substances, characterised by a prolonged or controlled release. One such object is achieved by a method for the preparation of a compact matrix as described above, in which the aforesaid uniform mixture of powders also comprises at least one active substance.

With the term "compressed unit" it is intended to indicated not only the conventional tablets for pharmaceutical use, in particular those for oral administration capable of releasing active substances or substances which restore physiological conditions, but also other devices obtainable by powder compression, for example urethral suppositories, tablets and disks for vaginal, buccal, nasal, dental, otological, ophthalmic or even epidermal application, capable of releasing active substances or substances which restore physiological conditions. The application of such tablets and devices must not be intended as limited to the sector of pharmaceutical products for human and veterinary use, where by active substance it is meant the medicinal substances according to the definition given respectively in the EU directive 2004/27 CE (art. 1) and 2004/28/CE (art. 1), but extended to other fields, such as that of medical devices according to the definition given in the EU directive 93/42/CEE, to that of the foods according to the definition given in art. 2 of the EU Regulations (CE) No. 178/2002, that of food supplements as defined by the directive 2002/46/CE, that of the dietary products and the products for infants as defined by the EU directive CE No. 89/398, that of the plant protection products, according to the definition given by the EU directive 91/414/CE, that of manure or fertilisers according to the definition and classification of the EU regulations (CE) No. 2003/2003, that of disinfectants and disinfestants and biocides in general according to the definition given in the EU directive 98/8/CE, that of detergents. Also radiopharmaceuticals, radionuclides and molecules marked with radionuclides can be carried and released by such matrix for diagnostic, therapeutic and general biocide purposes.

The aforesaid powder mixture can also comprise a diluent. The diluent preferably consists of anhydrous lactose (CAS RN 63-42-3) or monohydrate lactose (CAS RN 64044-51-5) in all the known amorphous and crystalline physical forms, also obtained by spray-drying or agglomeration like the TABETTOSE® and the PHARMATOSE DCL 15® and/or microcrystalline cellulose (for example AVICEL® PH, EMCOCEL®, TABULOSE®). Preformed mixtures of lactose/microcrystalline cellulose, such as for example a spray-dried compound containing 75% alpha-lactose monohydrate and 25% microcrystalline cellulose (MICROCELAC®) or CELLACTOSE®, or other excipients coprocessed for direct compression such as LUDIPRESS®, STARLAC®, PHARMATOSE® DCL 40, AVICEL® CE 15, Celocal, Proslov, can also be used.

The aforesaid alkylcellulose can be selected, for example, from the group comprising methylcellulose (CAS RN 9004-67-5) and ethylcellulose (CAS RN 9004-57-3) and the aforesaid hydroxyalkylcellulose can be selected, for example, in the group comprising hydroxypropylcellulose (CAS RN 9004-64-2 and RN 78214-41-2), hydroxypropylmethylcellulose (CAS RN 9004-65-3), hydroxyethylcellulose (CAS RN 9004-62-0), hydroxyethylmethylcellulose (CAS RN 9004-42-2).

It is also possible to use, in partial substitution of the alkyl- or hydroxyalkylcellulose, the following substances, also in combination with each other: Crospovidone, Povidone (9003-39-8), Vinylpyrrolidone-vinyl acetate copolymer (KOLLIDON® VA64), cellulose acetate phthalate (CAS RN 9004-38-0), Hypromellose phthalate (CAS RN 9050-31-1), Polyvinyl alcohol (CAS RN 9002-89-5), Polyvinyl acetate phthalate (CAS RN 34481-48-6), the various cyclodextrins (as described in the related monograph of the Handbook of Pharmaceutical Excipients fifth edition, Pharmaceutical Press), various types of methacrylate polymers also sold under the name of Eudragit (Rohm GmbH) such as those called E, L, S, RS, RL, PO, NE, RSPM, in the various types produced also by Eastman Chemical Company and BASF, glyceryl triacetate, triethyl citrate, acetyl tributyl citrate, dibutyl sebacate, diethyl phthalate, dibutyl phthalate, dioctyl phosphate, polyethylene glycol, polyethylene oxides (CAS RN 25322-68-3), calcium carboxymethylcellulose (CAS RN 9050-04-8), sodium carboxymethylcellulose (CAS RN 9004-32-4), Inuline (CAS RN 9005-80-5), Chitosan (CAS RN 9012-76-4) and its derivatives, Guar gum (CAS RN 9000-30-0), Xanthan gum (11138-66-2) and Tragacanth gum (CAS RN 900-65-1), Carbomer (CAS RN 9003-01-04 and 96827-24-6), Carrageenan (as described in the related monograph of the Handbook of Pharmaceutical Excipients fifth edition), Alginic acid (CAS RN 9005-32-7), Poloxamer (CAS RN 9003-11-6), Aliphatic polyesters (as described in the related monograph of the Handbook of Pharmaceutical Excipients fifth edition), Cellulose acetate butyrate, chitosan lactate, pectin, polyethylene-co-vinyl acetate, polyethylene, polyvinyl acetate-co-methacrylic acid, carnauba wax, butylated hydroxyanisole, ascorbyl palmitate, glyceryl palmitostearate, hydrogenated soybean and castor oil (Sterotek® K), glyceryl monostearate, d-.alpha.-tocopherol (Vitamin E), Vitamin E Succinate, Vitamin E and TPGS, Methyl Paraben, butyl stearate, stearyl alcohol, saccharose monopalmitate (Sucroester), glycerolesters and PEG esters (Gelucire 44/14), Polyoxyethylene alkyl ethers, Glyceryl palmitostearate Precirol® ATO 5, mineral oil, castor oil and excipients known for forming effervescent mixtures or systems. The aforesaid non-water-soluble, cross-linked polycarboxylic polymer that is swellable in water preferably consists of Polycarbophil (CAS registry number 9003-01-04).

The temperature at which the compressed units are heated is preferably in the range of 90-160° C. and the heating time is conveniently in the range of 1-30 minutes, in particular 1-20 minutes. The heating speed for bringing the compressed units to the treatment temperature can vary from 1° C./minute to 50° C./minute.

The compression of the powders to be subjected to the subsequent heat treatment can be conducted by working with pressures between 100-500 MPa. There can also be obtained compacts, with low tensile strength, to be subjected to subsequent heat treatment, by working at pressures between 5 kPa-100 MPa. The form of the compressed units can be any regular three-dimensional geometric shape, and the weight can vary according to needs and use (human or veterinary) up to exceeding 100 g for farming use.

These compressed units, in their composition, can be added, if necessary, with all of the adjuvants which are typically employed in the compression processes and known to those skilled in the art: glidants, lubricants, anti-adhesive agents, disintegrating agents and super-disintegrating agents, aromatizers, sweeteners and adsorbents.

Such tablets can be coated with the classical methods for polymer film-coating and/or dry coating (Pharmaceutical Dosage Forms: Tablets Volume 1,2,3, edited by H. A. Lieberman, L. Lachman, J. B. Schwartz, Dekker, second edition US 1989) in order to confer gastro-resistance, entero-solubility or environmental protection to the active substance.

The tablets that are the subject of this invention can be used as core or layer, containing or not containing the active substance, in order to obtain tablets known with the name of inlay tablets, multilayer tablets and core tablets (Pharmaceutical Dosage Forms: Tablets Volume 1, edited by H. A. Lieberman, L. Lachman, J. B. Schwartz, Dekker, second edition US 1989). The different additional layers can have qualitative composition identical to that herein stated and/or a different content of active substances or an additional active substance, or they can be different matrices that have already been described or employed in this field.

In the case of multilayer tablets, the matrix according to the invention, represents at least one layer of a multilayer tablet.

In the case of the core tablets, the matrix described here can represent the core or the crown layer, called outlayer, with or without active substance or with different active substances for every layer.

In the case of inlay tablets, the matrix according to the invention can represent both the outlayer and the inlay and can contain or not contain the active substance or several active substances. Even if the method according to the present invention is preferably a direct compression method, in certain situations, in order to overcome several drawbacks that the particle size of certain active substances could cause, the techniques known to those skilled in the art can still be used in the preparation of the tablets or the cores/inlay or of some layers. Such known techniques are called wet granulation (wet granulation, fluid-bed, granulation, spray-drying, spray-congealing) or dry granulation (dry granulation or roller compaction); or, possibly, the compression process can be applied to pellets subjected to a process, known as spheronization, which produces granules of spherical form and controlled size (Remington 21.sup.st edition, chapter 45, page 903). Naturally, the various granulation types require a minimum addition of adjuvants or excipients necessary for these process types and known to those skilled in this art. In the case of active substances susceptible to oxidation, the heating can be conveniently carried out in inert atmosphere, for example in nitrogen atmosphere.

For volatile or sublimable active substances, or in any case when necessary, the heat treatment can be carried out in a natural or an inert atmosphere, pressurizing such atmosphere up to 0.5 MPa above the environmental pressure. The cooling step after heating can occur naturally or in forced manner, for example controlling the cooling through the ventilation of dry air or inert gas (N2, Ar, He) at room temperature or dry air or inert gas cooled to temperature lower than room temperature.

After heating, a conditioning time can be necessary at environmental conditions before the packaging which, depending on the chosen composition, can even last 24 hours. Generally, such waiting time does not affect the quality of the production, but it is in any case preferable to wait a standard time of 5 minutes.

A preferred powder composition for use in the method according to the invention comprises active substance, MICROCELAC®, ethylcellulose and polycarbophil. Polycarbophil generally constitutes 5-35% by weight of the total weight of the powder mixture before compression and heat treatment, preferably 10-25%. Ethylcellulose and MICROCELAC® are generally present in the powder mixture in a weight ratio variable from 1:2 to 2:1 and preferably from 0.8:1 to 1.2:1, and constitute 45-95% by weight of the total weight of the mixture before compression and heat treatment, preferably 60-80%.

Ethylcellulose and polycarbophil are generally present in a weight ratio variable from 1:5 to 5:1. The active substance is contained in the powder mixture in a quantity variable from 0.001 ppm (parts per million) to 50% by weight of the total weight of the mixture before compression and heat treatment. In addition, within this percentage, the active substance can be mixed with suitable adjuvant substances for the solubilization process, forming hydrotropic complexes or inclusion complexes; or with substances promoting the processes of gastro-intestinal absorption or in any case the transmucosal absorption of drugs, known as enhancers; or substances which physically or chemically stabilise the active substance.

The active substance can be of natural origin, of synthesis or semi-synthesis with pharmacological action, employable for therapeutic, diagnostic or prophylactic use in humans or animals, or a substance of natural origin, of synthesis or semi-synthesis, biologically, physically or chemically active and employable for the care of the plant species (plant protection products), as fertiliser, as disinfectant and/or disinfestant of the person or the environment, or a substance belonging in general to the biocides category as defined by the EU.

The only condition required for the use of an active substance in the method according to the present invention is that it has a sufficient thermo-stability at the heating conditions (temperature, time) foreseen by the method itself. From the compressed units according to the present invention, substances can also be released having a nutritional power, as diet supplements for humans or animals, including both normal subjects and subjects affected with chronic or acute pathological conditions.

These compressed units can have use as cosmetic products, according to the definition of "cosmetic" as valid in the EU, if suitably formulated with substances permitted for cosmetic use.

The present invention also refers to a prolonged release tablet provided with bioadhesivity characteristics and comprising an active substance, at least one alkylcellulose or hydroxyalkylcellulose and a non-water-soluble, water-swellable cross-linked polycarboxylic polymer. Preferably, such a tablet has a controlled release and a release kinetics of the active substance substantially of zero order in an aqueous solution at pH 4-8.

The aforesaid tablet preferably also contains a diluent consisting of anhydrous or monohydrate lactose in all known crystalline and amorphous physical forms, and/or microcrystalline cellulose. It can also contain preformed mixtures of microcrystalline cellulose/lactose, known to those skilled in the art as one-body excipient, such as for example MICROCELAC®.

The variation of the ratios between the components indicated above, the compression conditions of the powders or granulates and the heating, temperature and thermal treatment time conditions allow to control the rate at which the release of the active substance occurs, which in general follows a zero order kinetics between pH 4 and 8.

If the active substance is absent (0%), such compressed and thermally treated matrix can still carry out, due to its capacity to swell in aqueous medium and its bioadhesive properties, a therapeutic action in several gastro-intestinal dysfunctions or in several pathologies like in chronic constipation, diverticulitis, irritable bowel syndrome and in all the other pathologies where these characteristics can be useful.

Such a tablet is obtainable with the above-illustrated method.

By exploiting the properties of these matrices, which after swelling in water reacquire their original shape and size through drying, several active substances, particularly those which are thermolabile or are difficult to obtain in the solid state, can be loaded in this matrix through imbibition, i.e. by soaking the matrices, according to the invention, prepared without the drug, in aqueous solutions with a suitable concentration of active substance. After a given time, the swollen tablets can be withdrawn and left to dry in air or through a suitable drying method, by forced ventilation with air or inert gas and possible mild heating, or through irradiation with IR lamp or through a lyophilisation process in order to re-obtain them in their original shape and size.

DETAILED DESCRIPTION OF THE INVENTION

Figure 1A:
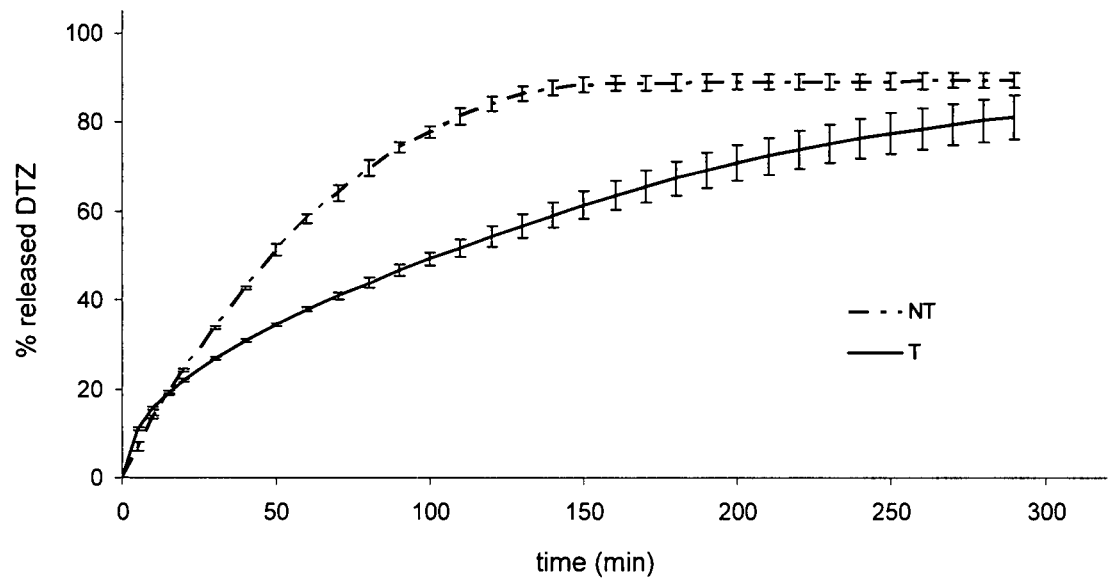
FIG. 1a shows the average dissolution profile (n=6) in 0.05 N HCl of Diltiazem (DTZ) released from tablets obtained with the method according to the present invention (example 1) (T) compared with tablets of identical composition but not subjected to heat treatment (NT). The bars represent the 95% confidence intervals.

The present invention originates from experimental work conducted on mixtures of different excipients useful for formulating tablets, in which the active substance release could be influenced by an energy treatment. The primary objective was that of obtaining tablets which, through a heating under atmospheric conditions, showed a prolongation of the release time, without showing degradations of the components of the formulation.

It was also sought to obtain a formulation from which the release of the active substance occurred from a non-easily erodible matrix according to a zero order kinetics, so that the release rate over time were independent of the residual quantity of active substance in the formulation, which is an essential requirement of the controlled release pharmaceutical forms.

In a first step, different formulations lacking drug were treated and, on the basis of the delay obtained in the disintegration times, the excipients were selected that were employed in the developed tablets. Afterwards, tests were conducted to evaluate the resistance of these excipients to the temperatures used for the energy treatment.

Then, a model drug was selected that might be useful for the characterization of the release from the tablets. The choice fell on Diltiazem hydrochloride, available on the market both in immediate or standard release preparations and in modified release formulations.

On the basis of the preliminary tests, and using this drug model, tablets of different composition were prepared.

The influence of the heat treatment on the active substance release from these tablets was evaluated by means of dissolution tests carried out both in an acidic medium, simulating the gastric environment, and in a phosphate buffer, which in part simulates the intestinal environment. The modifications undergone by the tablets were investigated through thermoanalytical techniques, spectroscopic techniques and through several physical tests typical for this type of pharmaceutical form.

Preparation of the Mixtures of Active Substance with the Various Excipients.

The mixing of the components, each optionally sieved, was carried out in amber-coloured, cylindrical glass containers with screw cap equipped with a Teflon stopper or in suitable stainless steel containers and was conducted in a TURBULA® mixer until the mixture of the components was completely uniform, generally in the following manner:

1. a core was formed composed of the minority component and an identical quantity by weight of active substance 2. the whole remaining active substance was added 3. The majority excipients were added in a weight amount identical to the weight amount of the powder contained in the container 4. The whole amount of the majority excipients was added.

For all the mixtures, each aliquot of powder was mixed for a time depending on the masses at stake, in general for the largest quantities up to a maximum of 30-40 minutes.

Preparation of the Tablets.

Tablets with a weight in the range of 150-170 mg were prepared by means of an alternating tabletting machine provided with concave monopunch.

Treatment of the Tablets and Powders.

The tablets subjected to treatment were positioned on a metal support, each one protected by a little metal mesh basket. The treatment was carried out in the oven of a gas chromatograph (HP 5890 series II) and consisted of heating to a predetermined treatment temperature and maintaining such temperature for a predetermined time. The temperature program employed was the following: 0.1 min at 25° C., reaching the final temperature with a gradient equal to 30°/min and maintenance of such temperature for the established time, then forced or natural cooling of the tablets to room temperature.

After treatment of every tablet, the percentage mass loss was evaluated ($\Delta$m %), according to the following equation:

$$\Delta.m\ \% = (m_o - m)/m_o * 100$$

where $m_o$ is the initial weight of the tablet and m is the weight of the same after heat treatment.

The treatment of the powders for the comparisons was carried out in the oven of the gas chromatograph in Pyrex glass tubes.

Storage of the Tablets.

The untreated and treated tablets were stored at room temperature in PVC blister pack for different periods: 47 days, 13 months and 32 months. At the end of the conservation period, the percentage increase in mass was evaluated, ($\Delta$w %), according to the following equation:

$$\Delta w\ \% = (m_c - m_o)/m_o * 100$$

where $m_c$ is the weight of the tablet after the storage period and $m_o$ is the initial weight of the same. For the treated tablets $m_o$ represents the weight after heat treatment.

Determination of the Tablet Hardness.

The test was carried out on treated and non-treated tablets by means of the appropriate instrument, considering as valid results only those deriving from an actual radial breaking of the tablet and not those due to deformation phenomena or capping. The obtained result represents the radial tensile strength and is expressed in kp (kilopond=kilogram-force=9.80665 Newton).

Determination of the Water Quantity Present in the Tablets.

The study was carried out by means of Karl Fischer (KF) titration with a suitable automatic apparatus (Mettler-Toledo DL38). As the titration agent, Hydranal Composite 5 (Riedel-deHaen) was used, standardised with sodium tartrate dihydrate (Riedel-deHaen). The obtained result was expressed in percentage (m/m) of water contained in a 55.0 mg powder sample, carefully weighed, deriving from the tablet crushed in glass mortar. Also in this case, the test was carried out on treated and untreated tablets.

Method for the Differential Scanning Calorimetry (DSC).

Physical Stability Studies on the Active Substances and the Excipients Used in the Formulation of the Tablets.

5.0 mg carefully weighed of every excipient/substance was placed in aluminium pans, closed with a suitable press and analyzed by means of DSC (Perkin Elmer 7) under nitrogen flow; the analysis was also carried out on the thermally-treated powders. The operating conditions utilised were the following: initial temperature ($T_{start}$)=50° C.; final temperature ($T_{end}$) 250° C.; gradient=10° C./min.

DSC Control on the Tablets Containing the Active Substance.

The tablets were ground in glass mortar and 5.0 mg, carefully weighed, of the powder obtained from each tablet was analysed in the above-described way. Also in this case, the test was carried out both on untreated tablets and on thermally treated tablets. All scans were carried out in nitrogen current.

Method for the Determination of the Mass Variations During Heating—Thermogravimetric Analysis (TGA)

The determination of the weight variations of the active substances and excipients, of the powder mixtures and the powders obtained by crushing the tablets was conducted through TGA 7 of Perkin Elmer, in nitrogen atmosphere, using the same temperatures and the same heating gradients used in the thermal heat treatments.

Disintegration Test.

The test was conducted by using an instrument in accordance with the monograph Disintegration of Tablets and Capsules of the European Pharmacopoeia 6th edition. The medium used, 1 L of deionized water, was maintained at the temperature of 37.+−.0.1° C. The test was carried out on 6 tablets at a time.

Dissolution Test.

The dissolution test was conducted in a device (Distek) in accordance with the monograph Dissolution Test for Solid Dosage Forms paddle apparatus of the European Pharmacopoeia 6th edition. The 1 L dissolution medium, contained in a glass vessel, was thermostated to 37.+−.0.1° C. and the rotation speed of the paddles was fixed at 50 rpm. The determination of the dissolved active substance was carried out through DAD UV-visible Agilent Technologies 8453, automated with peristaltic pump and tube-carrier system "Multi-cell Transport for Agilent 8453", controlled by the related software. After each reading, the dissolution medium was brought back into the starting vessel. The sampling time was fixed at 5 minutes for the first 20 minutes and then at 10 minutes up to 200 minutes and afterward fixed with a progression dependent on the total test time. The analysis was conducted at an analytical wavelength of 236 nm with a background subtraction window set between 450 and 600 nm. The determination was carried out by constructing a calibration curve in a concentration range which takes into account the dissolution of 1% and 100% of the theoretical content of active substance in the tablets.

The acidic dissolution medium consisted of a buffer prepared by adding deionized water to a suitable quantity of 37% HCl up to such a volume as to obtain a 0.05 N solution.

The dissolution medium at pH 7.2 consisted of a 0.05 M buffer phosphate, obtained by dissolving in deionized water the suitable quantities of sodium hydrogen phosphate dihydrate and potassium dihydrogen phosphate and adjusting the pH with suitable quantities of phosphoric acid or sodium hydroxide.

For every test, the dissolution profile was evaluated of 6 tablets.

IR Spectrometry.

The IR spectra of the different substances and mixtures were acquired through a Perkin Elmer 1310 spectrometer, preparing the samples in KBr disks.

Adhesion Tests.

Such measurements were carried out through a tensile tester (LLOYD LRX) modified for mucoadhesion measurements (Russo E, Parodi B, Caviglioli G, Cafaggi S, Bignardi et al. J Drug Deliv Sci Technol 14(6):489-494, 2004). In order to be able to carry out such test on a flat surface, cylindrical tablets were produced, having a weight of about 200 mg and a diameter of about 13 mm, applying a load equal to 2 tons per 1 minute with a manually actuated hydraulic press. Such presses are sold for preparing discs of KBr for the IR spectrometry. The substrate for the adhesion consisted of mucin tablets (Sigma) having a weight of about 250 mg and a diameter of about 13 mm prepared with a press for IR, by applying a load of 5 tons per minute.

The substrate for the adhesion was fixed to the load cell; the sample, fixed on the thermostated support at 37° C., was moistened with 200 µl of 0.05 M phosphate buffer at pH 7.2, also maintained at 37° C., for 1 minute.

A preload was applied of 1N for 2 minutes at a speed of 10 mm/min; for the evaluation of the adhesion, an elongation of 3 mm was set at the speed of 0.1 mm/s.

Interpretation of the Obtained Traces.

From the obtained graphs, the following parameters were obtained:

Maximum load [N];

Work [N·mm] obtained as integration of the elongation × load area;

Unit load [MPa] obtained from the ratio between the maximum load and the tablet area (132.73 mm$^2$).

The adhesion tests were carried out on tablets of only excipients (untreated and thermally treated) and on tablets containing active substance (untreated and thermally treated).

Evaluation of the Swelling Degree.

The tablets used were immersed in 0.05 M phosphate buffer at pH 7.2 thermostated to 37° C. and maintained under stirring by rotating blades at 50 rpm. Periodically (30 or 60 minutes), the tablets were drawn from the medium, drained on a metal grate for 30 seconds and weighed on an analytical balance. The swelling percentage degree, S %, was calculated according to the following equation:

$$S\% = (m_t - m_o)/m_o * 100$$

Where $m_t$ is the weight of the tablets drawn at time t and $m_o$ the initial weight of the tablets.

This test was carried out on tablets containing, or not containing, active substances that have been thermally treated, or have not been thermally treated.

Evaluation of the Volume of the Tablets.

The tablets were immersed in a graduated cylinder containing a known volume of Vaseline oil, The volume of such tablets was evaluated via difference with the initial liquid volume.

This test was carried out on treated tablets and on the same tablets after the dissolution test.

Many mixtures of different excipients were tested in order to solve the abovementioned technical problem, using Diltiazem hydrochloride (DTZ) as active substance model.

Several of the excipients tested are reported in the following Table 1.

TABLE 1

|  | Producers |
|---|---|
| Sodium starch glycolate (SAG) | Blanver, supplied by Giusto Faravelli S.p.A., Milan |
| MicroceLac ® (ML) | Meggle, supplied by Giusto Faravelli S.p.A., Milan |
| Crospovidone (Kollidon CL ®) (CPVP) | BASF, supplied by BASF Italy, Bergamo |
| Ethylcellulose (EC) | Hercules |
| Tablettose ® (TAB) | Meggle, supplied by Giusto Faravelli S.p.A., Milan |
| Microcrystalline cellulose (CM) | Blanver, supplied by Giusto Faravelli S.p.A., Milan |

TABLE 1-continued

|  | Producers |
|---|---|
| (Kollidon VA64 ® | BASF, supplied by BASF Italy, Bergamo |
| Hydroxypropylcellulose (Klucel 99 HF) (IPC) | Aqualon, supplied by Eigenmann & Veronelli S.p.A. |
| Methycellulose (Methocel A4C) (MC) | Supplied by Eigenmann & Veronelli S.p.A. |
| Cellulose acetate phthalate (CAF) | Fluka |
| Polyvinyl alcohol (PVA) | Sigma |
| β-cyclodextrin (β-CD) | Roquette, supplied by SPAD |
| Eudragit RSPM ® (EUD) | Rohm Pharma, supplied by Rofarma, Milan |
| Heptakis-trimethyl-β-cyclodextrin (tβ-CD) | Sigma |
| Polycarbophil (Noveon AA1) (POL) | Noveon, Cleveland (USA) |

With the above-reported excipients and the Diltiazem hydrochloride, mixtures were prepared with three, four and five components and from these tablets were prepared with the above-reported methods. The tablets were then subjected to the above-described tests and determinations.

It was verified that the desired results in terms of controlled release were obtained when the powder mixture comprised at least one of the components indicated in the annexed claim 1.

The effect of the thermal treatment involved by the method of the present invention on certain components of the obtained bioadhesive compact matrix was further investigated.

Figure 11:
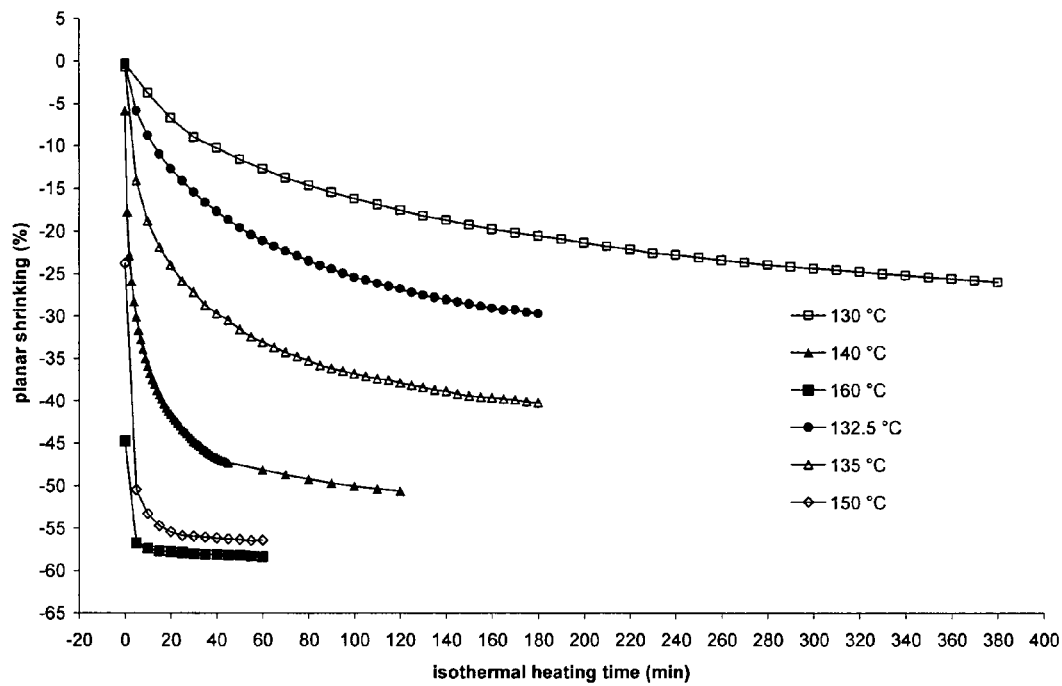
FIG. 11 is a graph showing the results of a hot stage microscopy study of percent planar shrinking of Polycarbophil powder subjected to different isothermal heating.

In FIG. 11 the results of a study on the thermal shrinking of Polycarbophil (shrinking versus heating time) are shown. As it can be seen from this figure, the maximum planar shrinking occurs when the Polycarbophil sample is heated at 160° C. for 5 minutes.

Figure 17:
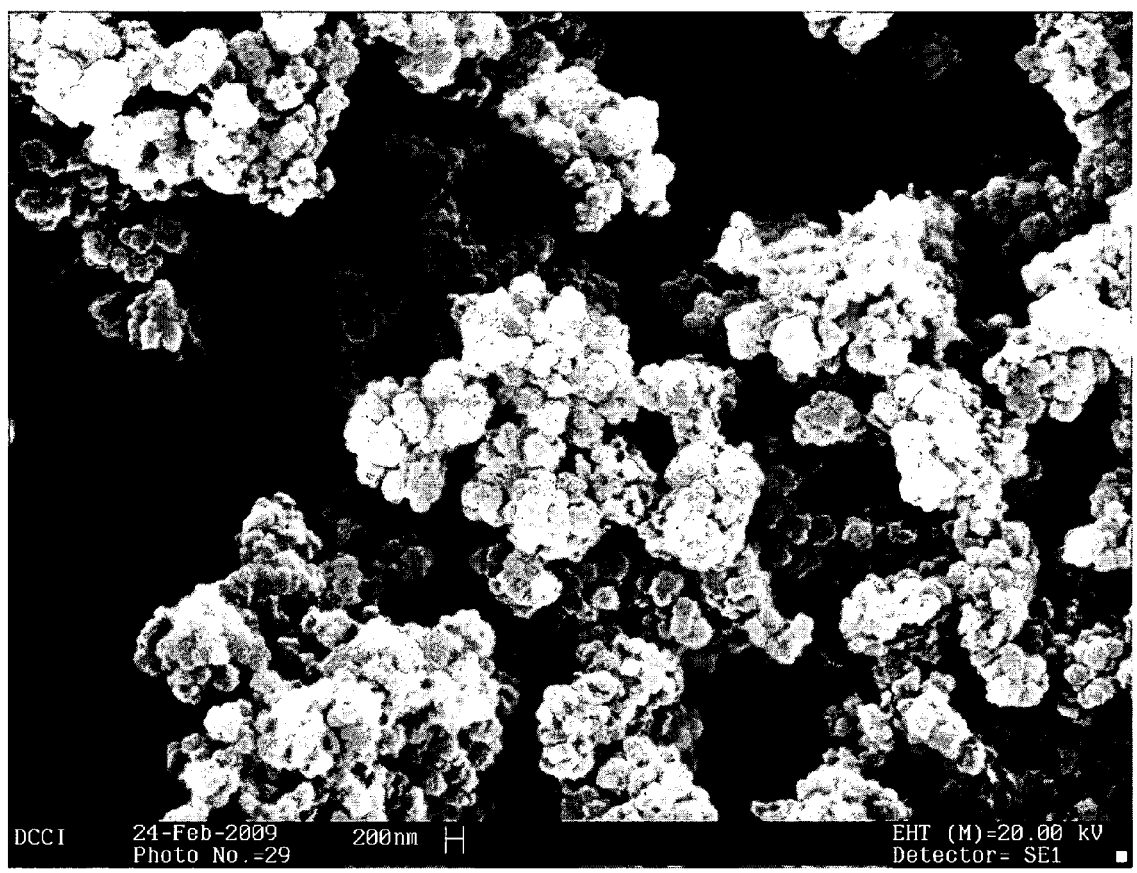
FIG. 17 is a SEM microphotograph of Polycarbophil powder that has not been subjected to any thermal treatment.
Figure 18:
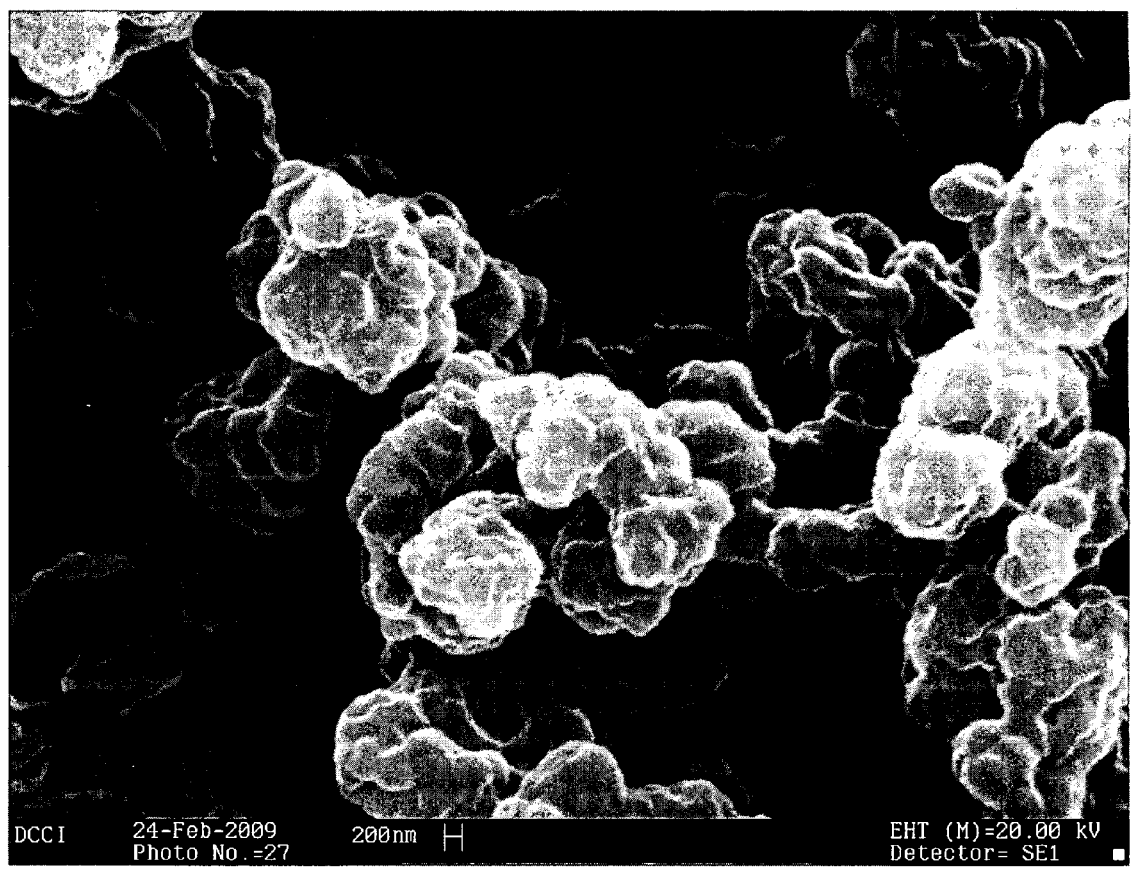
FIG. 18 is a SEM microphotograph of Polycarbophil powder subjected to heating at 150° C. for 15 minutes in a hot air oven.

The effect of the planar shrinking of the powder can be appreciated from the SEM microphotographies of FIGS. 17 and 18. In FIG. 17 a bunch of grapes-like morphology is shown, whereas the individual grapes disappear in FIG. 18, where one can rather appreciate formations having a continuos matrix (looking like a rose) and a smaller overall volume: this is the consequence of the thermal treatment that the powder has been subjected to. Moreover, one can observe in FIG. 18 bridges connecting the individual granules, whereas the granules of FIG. 17 are clearly separated from each other.

Figure 12:
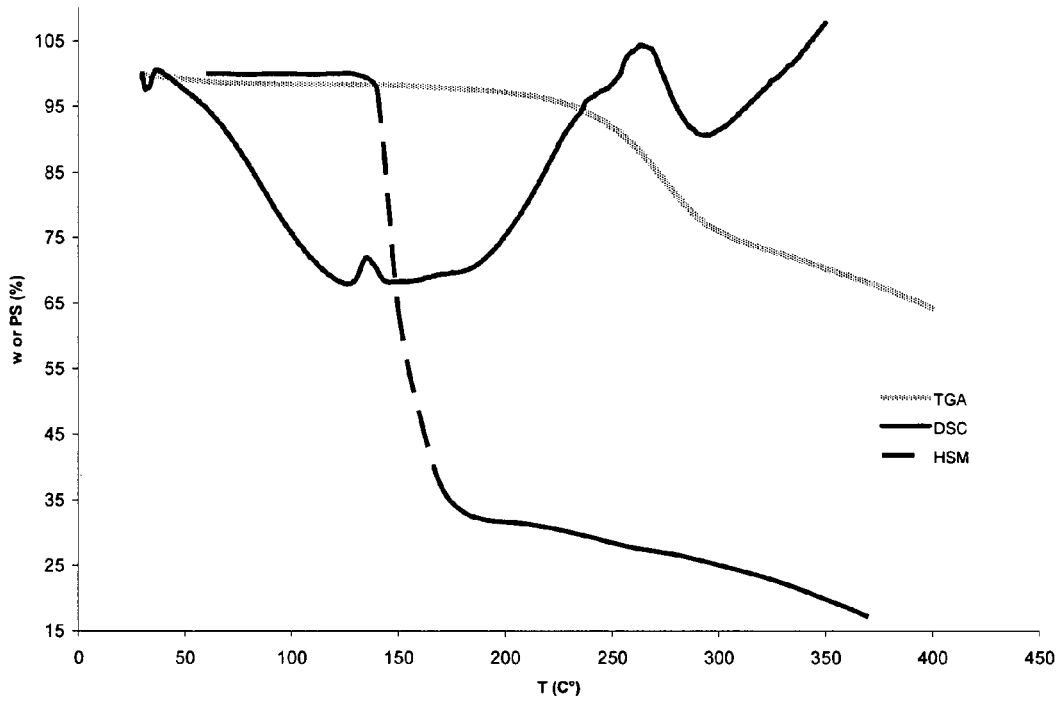
FIG. 12 shows a comparison of DSC profile (endo up), TGA profile (weight percent against temperature) and hot stage microscopy (HSM) profile of % planar shrinking (PS) against temperature of Polycarbophil powder.

In the graph of FIG. 12, the three superimposed profiles (DSC, TGA and HSM) show that the shrinking phenomenon, measured as planar shrinking on the focus plane of the microscope, is not linked to any phenomena of Polycarbophil degradation, but is probably linked to the endothermal events occurring in the Polycarbophil above 50° C. and reaching their peak with a small endothermic curve between 128° C. and 147° C.

Figure 13:
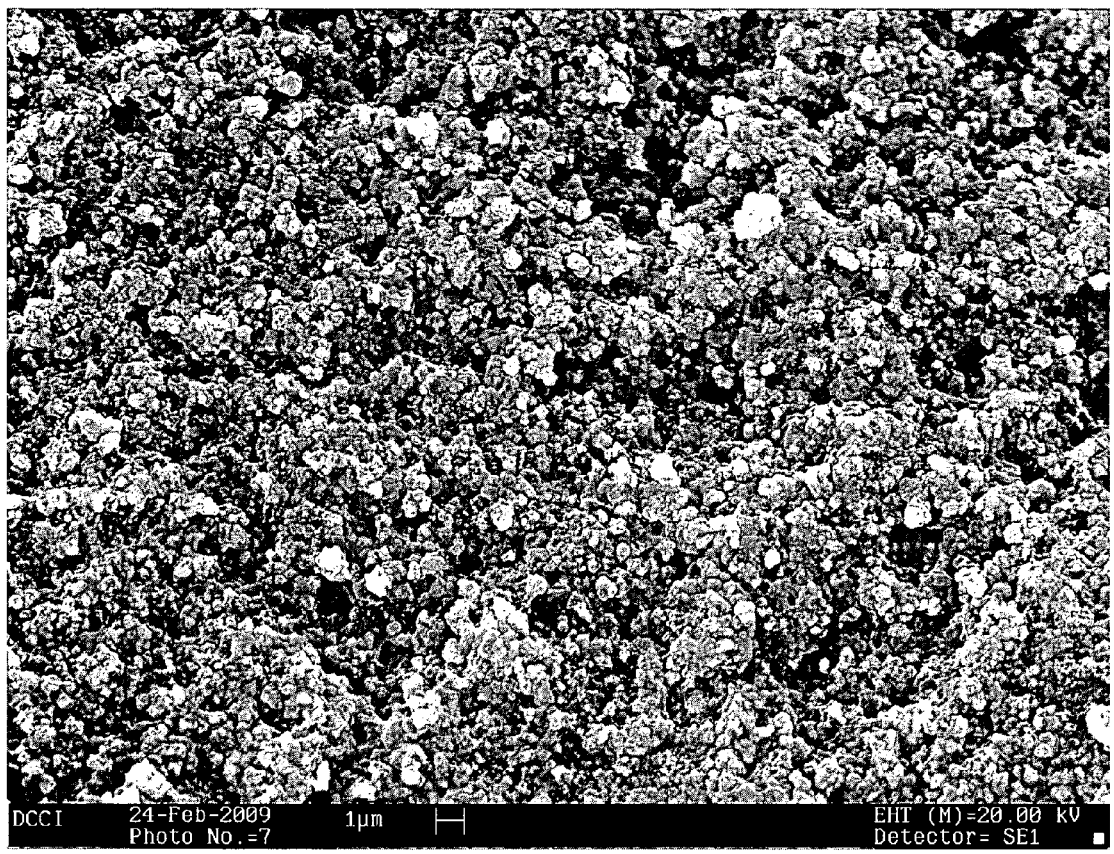
FIG. 13 is a SEM microphotograph of a cross-section of a Polycarbophil compact (not subjected to thermal treatment). The compact was obtained by applying a 750 kPa pressure for 15 min on 100 mg Polycarbophil powder.
Figure 14:
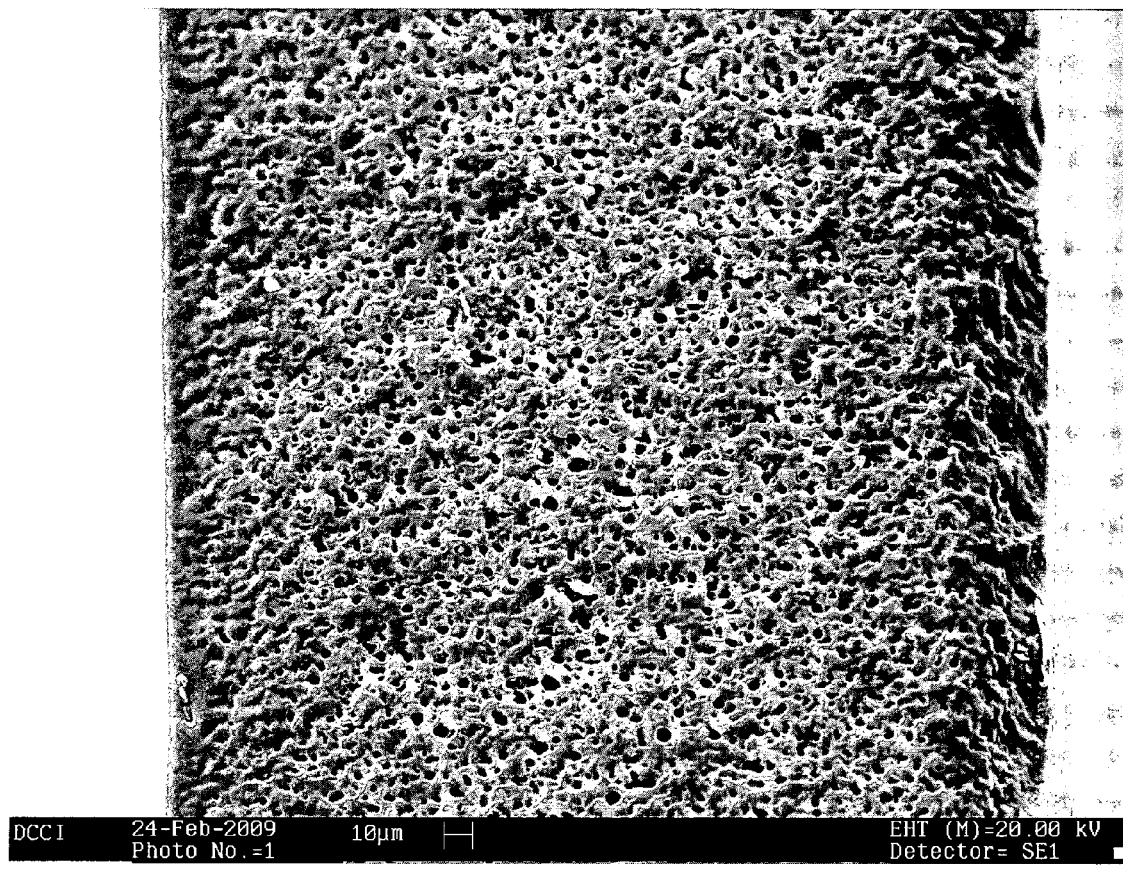
FIG. 14 is a SEM microphotograph of a cross-section of a thermally treated Polycarbophil compact. The compact was obtained by applying a 750 kPa pressure for 15 min on 100 mg Polycarbophil powder, The compact was then subjected to heating at 150° C. for 15 min in a hot air oven.

From a comparison of the SEM microphotographies of FIGS. 13 and 14, one can clearly appreciate that when a Polycarbophil compact is subjected to a thermal treatment (150° C. for 15 minutes), its structure dramatically changes: in FIG. 14 a trabecular matrix is quite apparent, whereas nothing similar is visible in FIG. 13.

Figure 15:
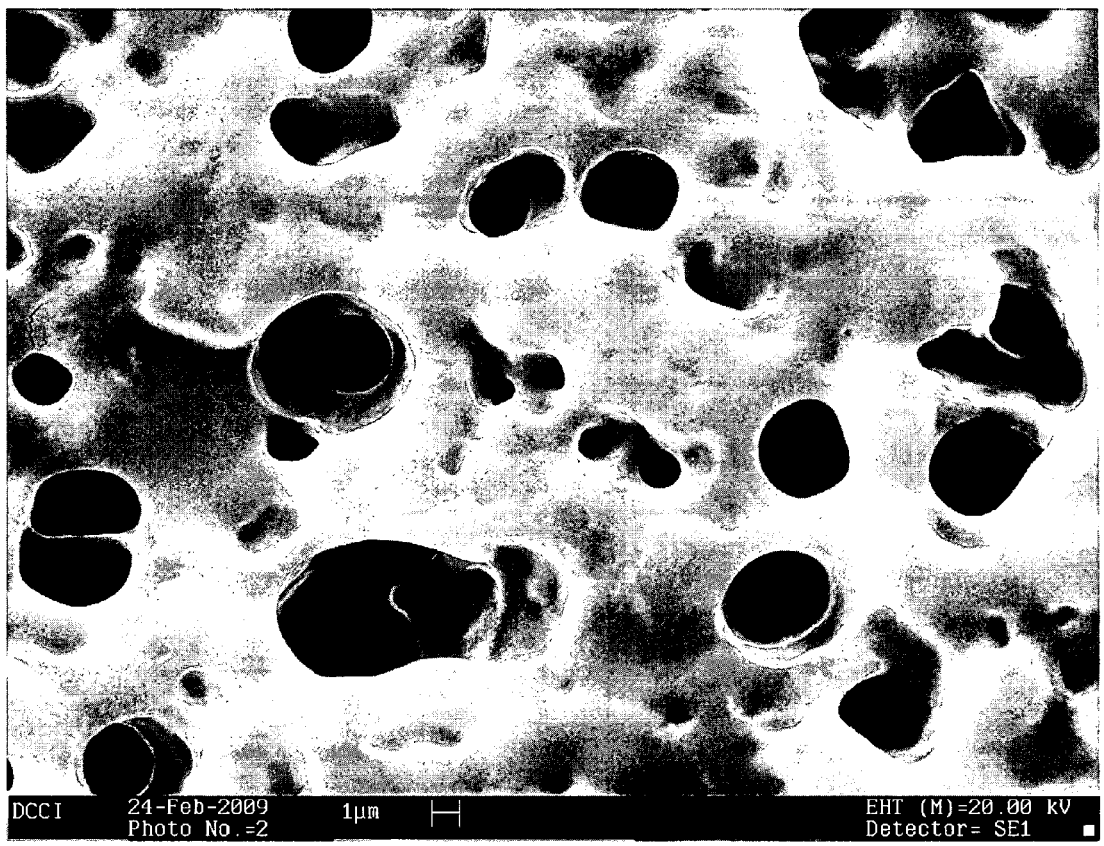
FIG. 15 is a SEM microphotograph of the same sample of FIG. 14 at a higher magnification.
Figure 16:
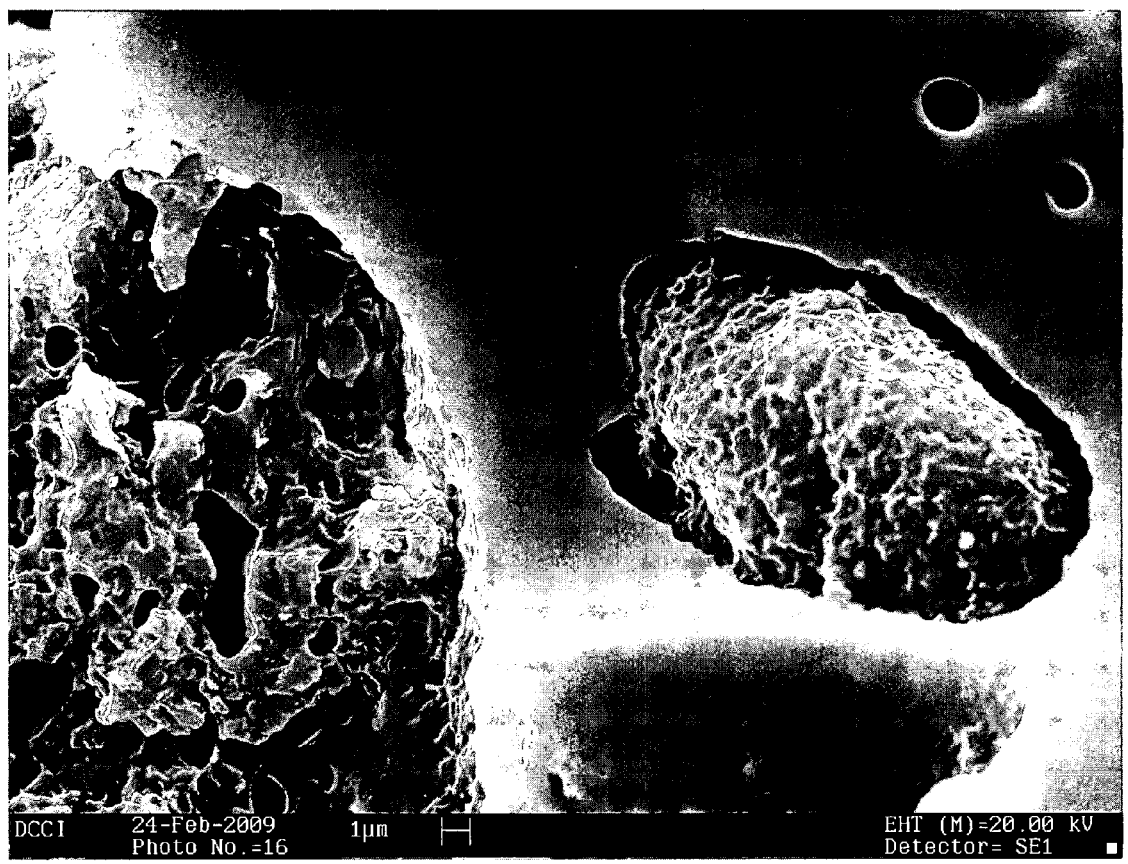
FIG. 16 is a SEM microphotograph of a cross-section of a thermally treated compact of Ethylcellulose/Polycarbophil 3:2. The compact was obtained by applying a 750 kPa pressure for 15 min on 100 mg of a powdery mixture of Ethylcellulose/Polycarbophil 3:2. The compact was than subjected to heating at 150° C. for 15 minutes in a hot air oven.

The trabecular matrix and the pores that are included in such matrix can further be appreciated from the enlarged magnification photograph of FIG. 15. The combined effect of compression and heating has also been studied on a mixture of Ethylcellulose and Polycarbophil (3:2). As it can be seen from the microphotograph of FIG. 16, the interaction between the two polymers gives rise to the partial occlusion of two Ethylcellulose microgranules in the pores of the newly formed Polycarbophil matrix.

Reported below, as exemplifying and non-limiting, are several examples of compositions adapted for being employed in the method according to the present invention, containing in addition to Diltiazem hydrochloride (DTZ) also Gliclazide (GLZ).

Example 1

The following components were mixed according to the above-illustrated operating methods until a uniform powder was obtained:

| | |
|---|---|
| Diltiazem hydrochloride | 20% |
| Ethylcellulose | 35% |
| MicroceLac | 35% |
| Polycarbophil | 10% |

The percentages indicated in the text of the present application, where not otherwise specified, must be understood as percentages by weight of the total weight of the powder mixture before compression and before heat treatment. From this powder mixture, tablets were prepared by direct compression according to the above-illustrated procedure.

A part of these tablets was subjected to a heat treatment with the above-illustrated modes, keeping them at the treatment temperature of 150° C. for a treatment time of 15 minutes. After such time had elapsed, the oven was immediately cooled to room temperature by means of forced ventilation. Minimum conditioning time at room temperature before packaging: 5 minutes. The non-thermally treated tablets (sample n=20) had an average water content, according to KF, equal to 2.57% (standard deviation sd=0.09) weight/weight tablet and an average hardness of 307.8 N (31.4 kp; sd=1.2) while those thermally treated (sample n=20) had a water content equal to 0.88 (sd=0.08) and a hardness of 405.9 N (41.4 kp; sd=1.1).

The thermally-treated tablets (called T) showed the dissolution profile in 0.05 N HCL represented in FIG. 1a, in which the dissolution profile is also represented of the corresponding non-thermally treated tablets (called NT).

The curves represent the average values of six non-treated tablets and six thermally treated tablets.

The modification produced by the thermal treatment of the tablets is clear from FIG. 1a, with regard to the release of the Diltiazem hydrochloride in acidic environment. The heat treatment acts on the components of the tablet, generating a matrix which considerably slows the release of the drug, which occurs by following a zero order kinetics.

In the initial phase, before reaching 20% drug release, the releases from both the tablets seem to overlap each other, probably due to a burst effect that precedes the hydration and gelling of the matrices of the tablets T. In the first phase, the release of the treated tablets in any case seems slightly faster, in fact after 30 minutes the matrix releases over 11%.

Figure 1B:
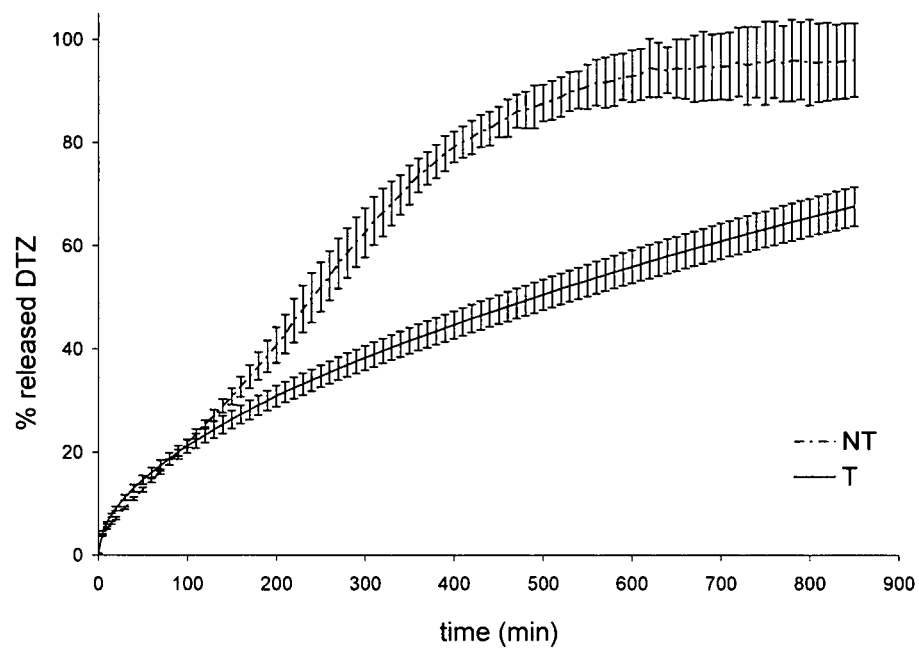
FIG. 1b shows the average dissolution profiles (n=6) in phosphate buffer (pH 7.2) of Diltiazem (DTZ) released from tablets obtained with the method according to the present invention (example 1) (T) compared with DTZ released from tablets of identical composition but not subjected to heat treatment (NT). The bars represent the 95% confidence intervals.

In FIG. 1b, the dissolution profile is reported in phosphate buffer (pH=7.2) of the tablets T compared with that of the corresponding NTs.

Here too, the curves represent the average values of six non-treated tablets and six thermally treated tablets.

The effect of the treatment on the DTZ release in phosphate buffer is even more evident, The matrix which is generated after such treatment releases the drug much more slowly; indeed, between 100 and 850 minutes it releases about 47% of the loaded drug. The $t_{50}$ (time in which 50% of the drug is released) is equal to 4 hours for the NTs, while for the Ts it is equal to about 14 hours. In fact, the Ts after 4 hours release only 33% of the loaded drug, and after 850 minutes they have not yet reached the maximum release of the loaded DTZ.

Also in this buffer, the tablets T have a release which follows a zero order kinetics after a brief initial period of adjustment connected with the burst effect.

Figure 9:
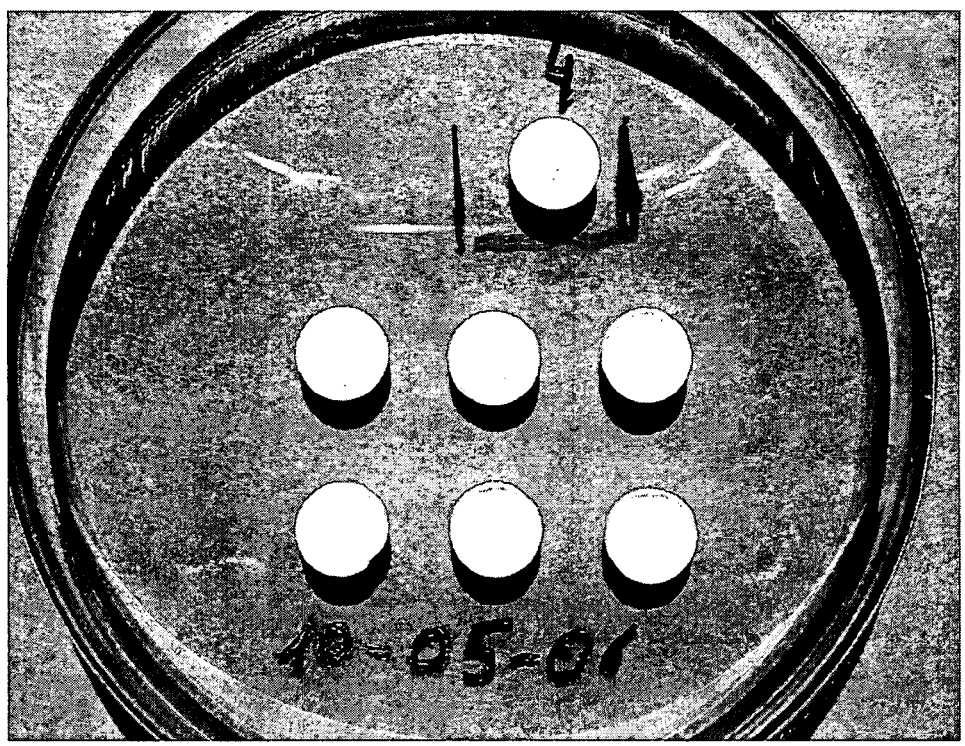
FIG. 9 shows a comparison between the size of a thermally treated (150° C. for 15 minutes) tablet according to the present invention (example 2) stored in blister pack for 38 months and that of 6 tablets of the same batch, which underwent a dissolution test in 0.05 N HCl after thermal treatment (150° C. for 15 minutes) and storage for 13 months in blister pack, were then subjected to drying with air at room temperature and finally, after such drying at room temperature, were stored in air for further 25 months.

At the pH of the phosphate buffer, the matrix formed in the tablets T following the heat treatment absorbs the aqueous dissolution medium, swelling and thus increasing its volume, forming a gelatinous outside layer (see FIG. 7a, last towards the right), due to which the drug release mechanism is actuated according to a zero order kinetics. It is moreover observed that the swollen matrices of the tablets that underwent the heating process remain integral, i.e. they do not undergo erosion phenomena during the entire dissolution test (see also swelling) and once recovered and left to dry they reacquire the shape and size of the tablets from which they originated, similarly to what happens for example 2 (FIG. 9).

Similarly to what happens for example 2 (FIG. 10), also in acidic environment it is observed, to a lesser degree, the formation of a gelatinous crown, The comparison with the NT tablet allows confirming that the heat treatment on the component mixture forms a non-erodible matrix which releases the drug by maintaining the release rate constant (% released/release time) for a prolonged time period. In addition, a gelled and translucent crown is visually observable—which is probably responsible for the control of the drug release—, which forms from this particular matrix through a gradual swelling phenomenon.

The control of the release rate can be attributed to both the matrix swelling phenomenon and the molecular diffusion of the drug, dissolved in the aqueous medium which makes the matrix swell, through the gelled layer of the matrix. Such phenomena are not observable in the NT tablets, which at the end of the dissolution test were completely disintegrated.

The formation of a modification correlated with the formation of the matrix is also evident from the increase of tablet hardness of 98.04 N (10 kp).

Figure 1C:
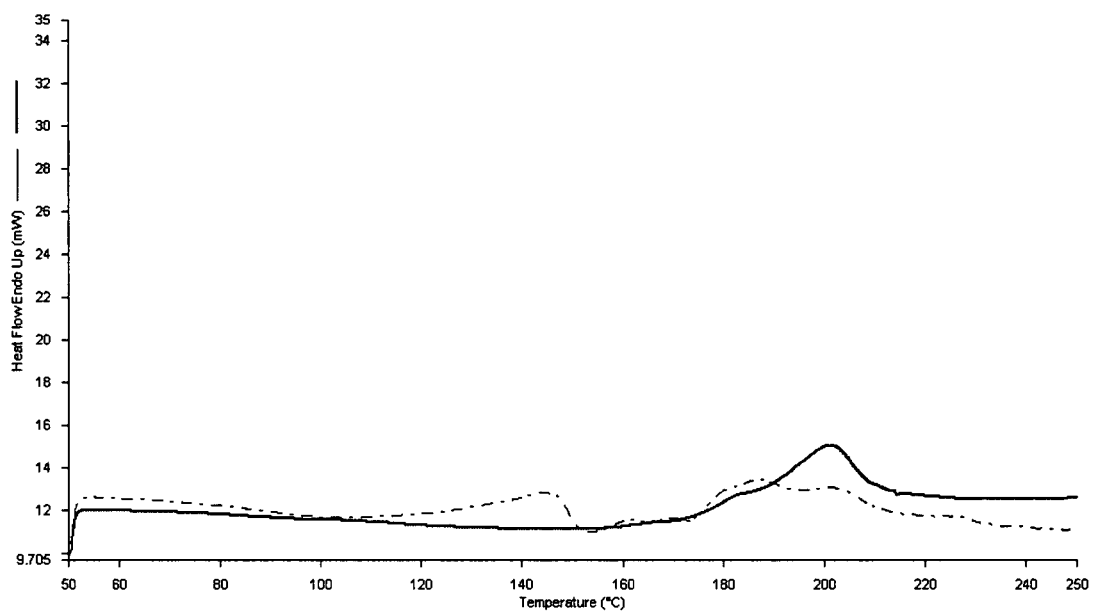
FIG. 1c shows the DSC profile (solid line) of thermally treated (150° C. for 15 minutes) tablets obtained with the method according to the present invention (example 1) compared with the DSC profile of tablets of identical composition but not subjected to heat treatment (dashed line).

The transformations induced by the heat treatment generating the matrices are shown by the DSC trace as in FIG. 1c.

Example 2

The following components were mixed according to the operating procedures illustrated above in order to obtain a uniform powder:

| | |
|---|---|
| Diltiazem hydrochloride | 20% |
| Ethylcellulose | 30% |
| MicroceLac | 30% |
| Polycarbophil | 20% |

From this powder mixture, tablets were prepared by direct compression according to the above-illustrated procedure.

A part of these tablets was subjected to a heat treatment in the above-illustrated way, keeping them at the treatment temperature of 150° C. for a treatment time of 15 minutes. After such time had passed, the oven was immediately cooled to room temperature by means of forced ventilation. Minimum conditioning time at room temperature before packaging: 5 minutes.

The non-thermally treated tablets (sample n=20) had an average water content, according to KF, equal to 2.57% (standard deviation sd=0.08) weight/tablet weight and an average hardness of 247.1N (25.2 kp) (sd=1.3), while those thermally treated (sample n=20) had an average water content equal to 1.26 (sd=0.05) and a hardness of 401.0 N (40.9 kp) (sd=1.1).

Figure 2A:
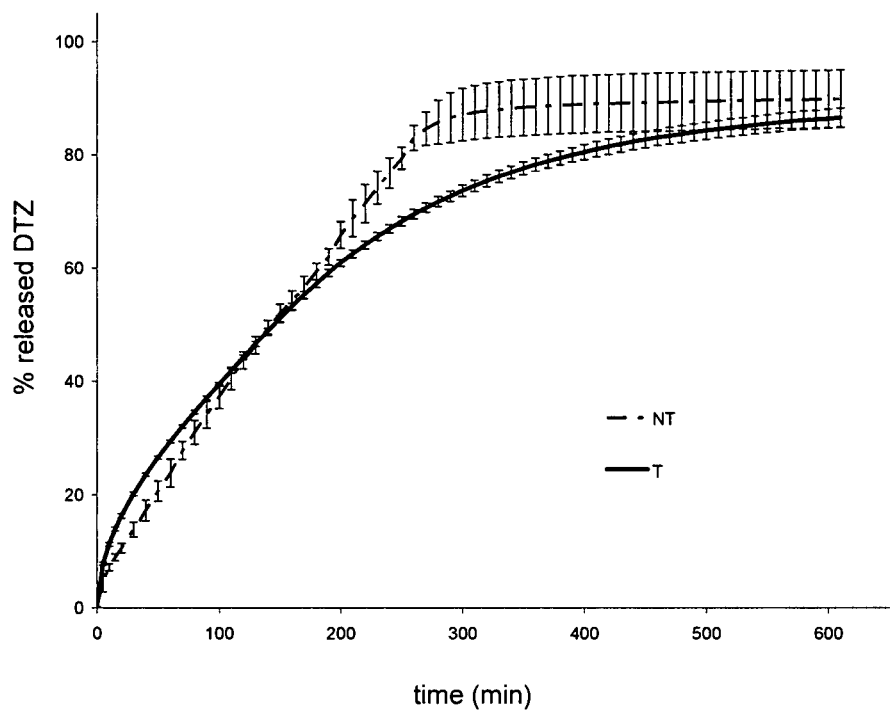
FIG. 2a shows the average dissolution profiles in 0.05 N HCl of Diltiazem (DTZ) released from tablets obtained with the method according to the present invention (example 2) (T) compared with DTZ released from tablets of identical composition but not subjected to heat treatment (NT). The bars represent the 95% confidence intervals.

The thermally treated tablets (T) showed the dissolution profile in 0.05 N HCl represented in FIG. 2a, in which the dissolution profile of the corresponding non-thermally treated tablets (NT) is also represented.

The curves represent the average values of six non-treated tablets and six thermally-treated tablets.

In FIG. 2a, the considerable prolongation of the DTZ release is observed which can be obtained following heat treatment of these tablets. The effect of the heat treatment on the different quantitative composition of this example is clearly seen—in this example, the Polycarbophil content is doubled. This is reflected on the release of the DTZ in acidic environment. A greater prolongation of the release is observed, which does not reach its maximum even after 10 hours, while the NT tablets reach their maximum after 5 hours. At the same time, the initial release becomes faster with respect to that of the NTs; one can see a release which follows a zero order kinetics between 40 and 210 minutes.

Figure 2B:
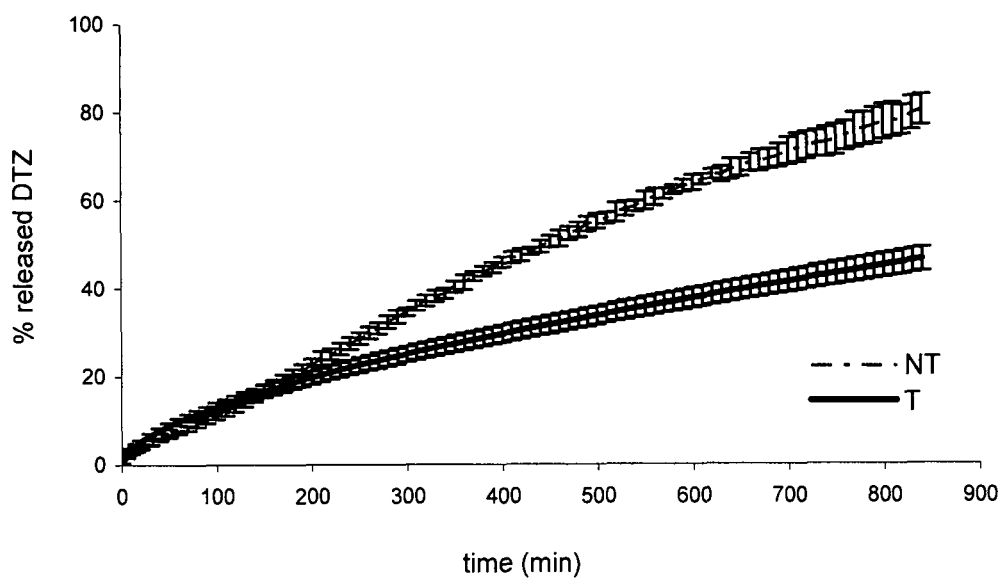
FIG. 2b shows the average dissolution profiles (n=6) in phosphate buffer (pH 7.2) of Diltiazem (DTZ) released from tablets obtained with the method according to the present invention (example 2) (T) compared with DTZ released from tablets of identical composition but not subjected to heat treatment (NT). The bars represent the 95% confidence intervals.

In FIG. 2b, the dissolution profile is reported in phosphate buffer (pH=7.2) of six thermally treated tablets T compared with that of six corresponding non-treated tablets NT.

Each curve represents the average value of the six tablets, while the vertical bars represent the 95% confidence interval.

As for the preceding example, the treated tablets have a release which follows a zero order kinetics, established after brief initial adjustment period. The increase of the Polycarbophil content determines a further reduction of the release rate with respect to the preceding example, in fact after 840 minutes of dissolution, the NTs release 80% of the loaded drug, while the Ts release about 41%. The latter release after 1400 minutes (FIG. 3C) about 66% of the loaded drug.

Also in this case, it is observed during the test, in the thermally treated tablets, a volume increase along with the formation of a crown of translucent gelled material, more transparent with respect to example 1, which surrounds a very visible solid core (see FIGS. 7a central photograph; 7b, 7c), containing the drug quantity not yet dissolved.

Figure 10:
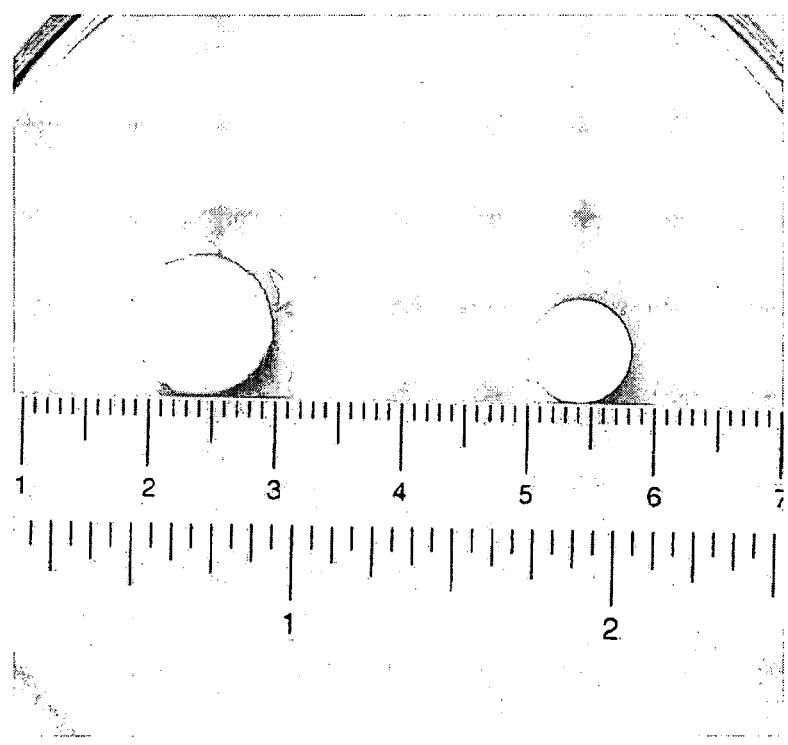
FIG. 10 shows a comparison between thermally treated (150° C. for 15 minutes) tablets according to example 2, at the maximum swelling degree reached at the end of the dissolution test in 0.05 N HCl and a tablet in its original size. In particular, on the left, a tablet is illustrated according to example 2 at the maximum swelling degree reached at the end of the dissolution test in 0.05 N HCl at 37° C. On the right, a tablet is illustrated according to example 2 of original size.

The formation of a gelled crown, smaller with respect to that which is formed in the dissolution at pH 7.2, can also be seen in the dissolution at acid pH (FIG. 10). FIG. 9, related to tablets obtained according to the present example, demonstrates that, as reported above, the tablets according to the present invention, after swelling in water, reacquire their original shape and size upon drying. This allows extending the application of the method according to the present invention also to active substances that are thermolabile or difficult to obtain at the solid state, which can be loaded by means of imbibition with aqueous solutions of such substances of a compressed matrix lacking active substance obtained with the present method, then proceeding with the drying of the impregnated and swollen matrix.

The increase of the hardness of the tablets which underwent the heat treatment represents as in example 1 proof of the formation of the matrix inside the tablet. In this example, the average increase of the hardness is greater than that of the preceding example, equal to 135.3 N (13.8 kp), and is probably correlated with the different consistency of the gel of the hydrated matrix which surrounds the solid core and which is reflected on the reduction of the release rate registered by the dissolution test.

Figure 2C:
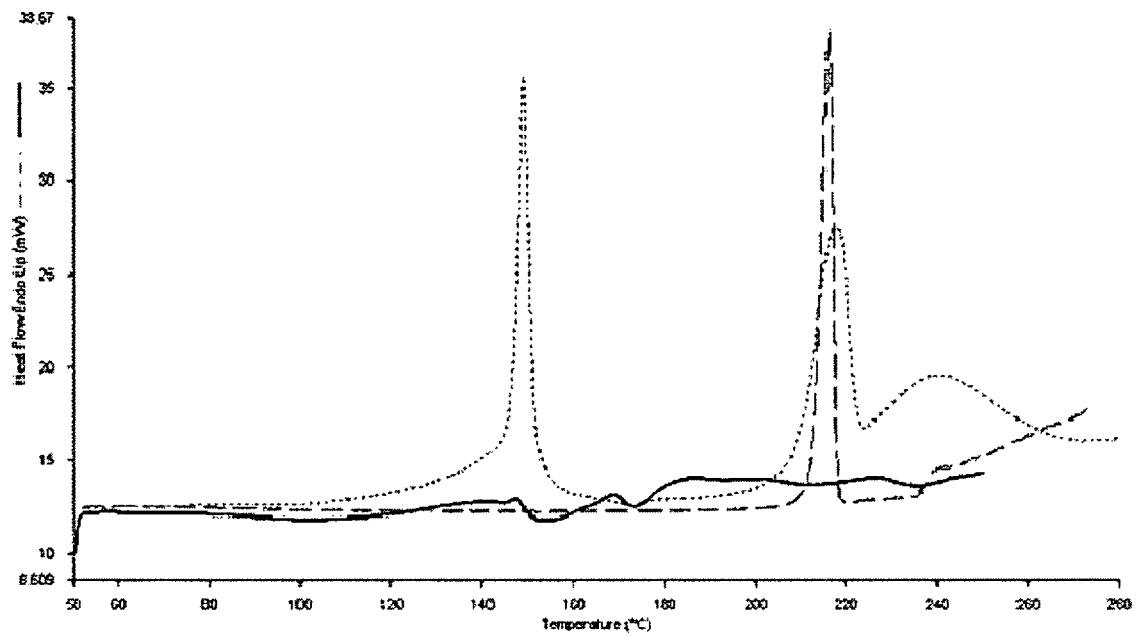
FIG. 2c has, below, a DSC trace of tablets obtained according to the present invention (example 2) (solid line) compared with the trace of tablets of identical composition but not thermally treated. Above, there are the DSC traces of Diltiazem (dashed line) and MicroceLac® (dotted line) compared with the DSC trace of tablets of identical composition to that of the tablets according to example 2 but not thermally treated (solid line).
Figure 2C:
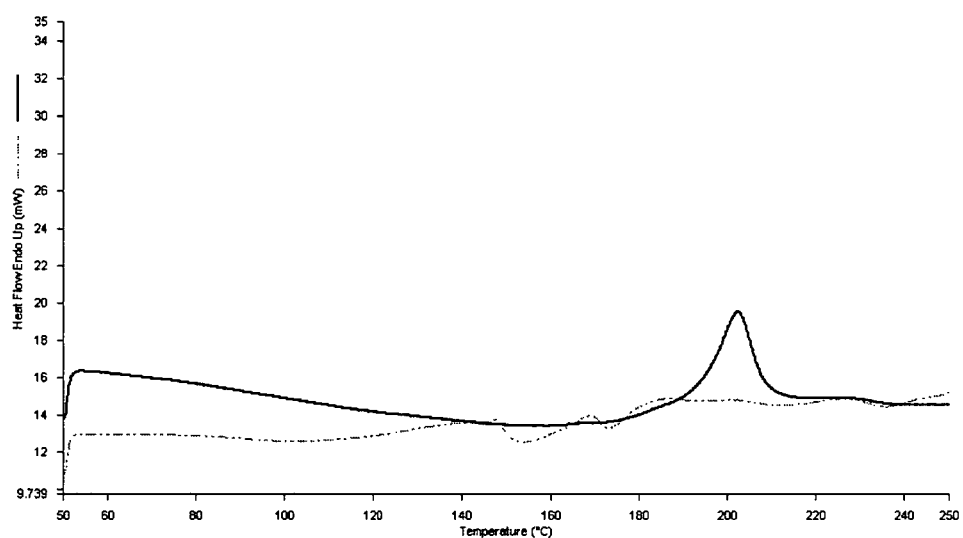

FIG. 2c is a DSC trace, obtained with the above-reported modes, of tablets T compared with the DSC trace of tablets NT. In the upper part, the DSC traces of the physical mixture of the powders of the present example, of the MicroceLac (ML) and Diltiazem hydrochloride (DTZ) are reported.

The transformations induced by the heat treatment generating the matrices are shown by the DSC trace as in the lower part of FIG. 2c.

Example 3

The following components were mixed according to the operating methods illustrated above in order to obtain a uniform powder:

| | |
|---|---|
| Diltiazem hydrochloride | 40% |
| Ethylcellulose | 22.5% |
| MicroceLac | 22.5% |
| Polycarbophil | 15% |

From this powder mixture, tablets were prepared by direct compression according to the above-illustrated procedure.

A part of these tablets was subjected to a heat treatment in the above-illustrated way, keeping them at the treatment temperature of 150° C. for a treatment time of 15 minutes, After such time had passed, the oven was immediately cooled to room temperature by means of forced ventilation. Minimum conditioning time at room temperature before packaging: 5 minutes.

The non-thermally treated tablets (sample n=20) had an average water content, according to KF, equal to 3.14% (standard deviation sd=0.1) weight/tablet weight and an average hardness of 236.3 N (24.1 kp; sd=0.8), while those thermally treated (sample n=20) had an average water content equal to 1.26 (sd=0.09) and a hardness of 259.8 N (26.5 kp; sd=1.4).

Figure 3A:
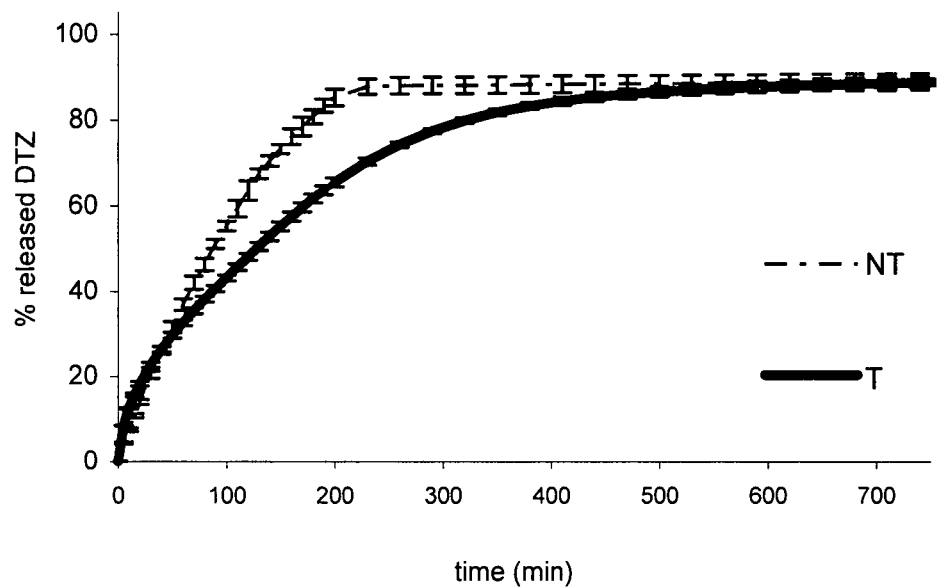
FIG. 3a shows the average dissolution profiles (n=6) in 0.05 N HCl of Diltiazem (DTZ) released from tablets obtained with the method according to the present invention (example 3) (T) compared with DTZ released from tablets of identical composition but not subjected to heat treatment (NT). The bars represent the 95% confidence intervals.

The thermally treated tablets (T) showed the dissolution profile in 0.05 N HCl represented in FIG. 3a, in which the dissolution profile of the corresponding non-thermally-treated tablets (NT) is also represented.

Every curve represents the average value of the dissolution profile of six tablets, while the vertical bars represent the value of the 95% confidence interval.

Figure 3B:
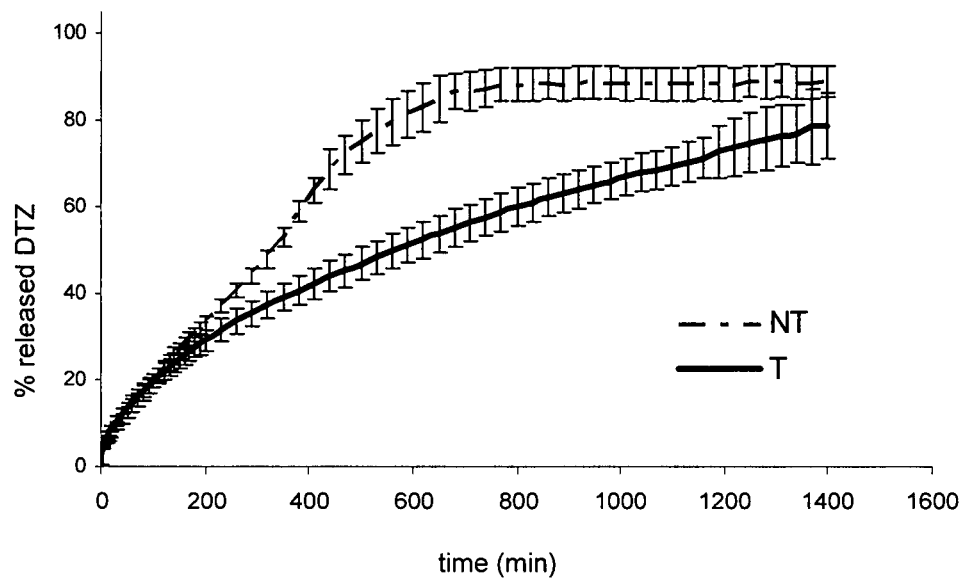
FIG. 3b shows the average dissolution profiles (n=6) in phosphate buffer (pH 7.2) of Diltiazem (DTZ) released from tablets obtained with the method according to the present invention (example 3) (T) compared with DTZ released from tablets of identical composition but not subjected to heat treatment (NT). The bars represent the 95% confidence intervals.
Figure 3C:
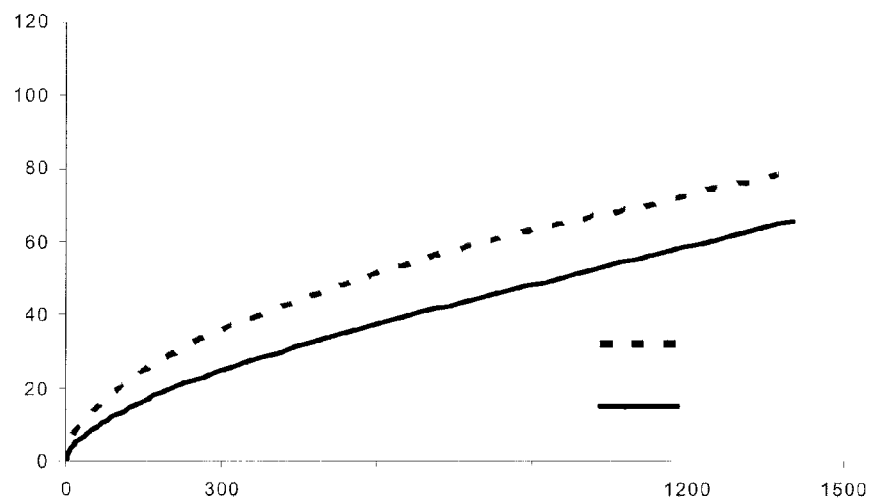
FIG. 3c presents a comparison between the average dissolution profiles (n=6) in phosphate buffer (pH 7.2) of Diltiazem (DTZ) released from 6 tablets according to example 3 and from 6 tablets according to example 2.

In FIG. 3b, the dissolution profile is reported in phosphate buffer (pH=7.2) of the thermally treated tablets (T) compared with that of the corresponding non-treated tablets (NT). Here too, the curves represent the average values of six non-treated tablets and six thermally treated tablets.

It can be seen from the dissolution profiles how, even when doubling the drug loading (with respect to the previous examples), the matrix that is the subject of the patent continues to control the release of the drug. The effect of the heat treatment is, as in the previous cases, more evident in phosphate buffer than in HCl. The release kinetics, after an initial phase, becomes zero order, as attested by the rectilinear progressions of the dissolution profiles, except for the non-treated tablets (NT) whose profile in phosphate buffer deviates from linearity, probably due to erosion phenomena which precede the complete disintegration of the tablets.

In acidic environment, the tablets T release the drug more readily in the first 30 minutes, then zero order kinetics are established in which about 50% of the loaded DTZ is released. The release for the tablets T is completed after about 400 minutes, while the NTs complete it within 230 minutes.

In phosphate buffer, the tablets NT attain complete release after about 560 minutes, while the tablets T attain it after 1400 minutes.

Also in this case, a swelling of the treated tablets is observed that, after having undergone the dissolution test in HCl, remain integral; after the test in phosphate buffer, the tablets are swelled to a much greater extent and are surrounded by a gelatinous layer, and are capable of recovering their original shape after having been recovered and dried.

The comparison is quite interesting (FIG. 3c) between the dissolution profiles in phosphate buffer of this example and the analogous profile of Example 2. From the parallelism between the linear sections of the two profiles, one can infer that the matrix of example 3, generated with a composition having the same EC/Polycarbophil ratio as example 2, is able to control the DTZ release with the same rate as that example, even when the drug loading is doubled. Of course, the burst effect is greater in example 3.

Figure 3D:
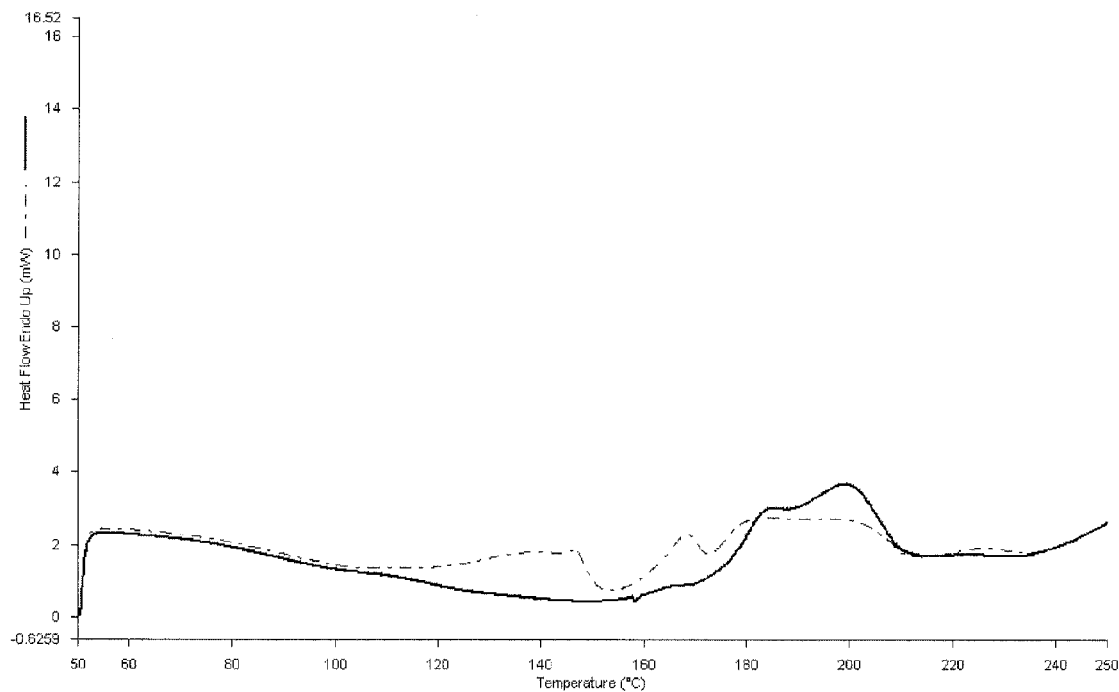
FIG. 3d shows, in comparison to one another, the DSC traces of tablets according to example 3 (solid line) and of tablets of identical composition but not thermally treated (dashed lines).

FIG. 3d shows a DSC trace, obtained in the above-mentioned way, of tablets T compared with the DSC trace of NT tablets. The transformations induced by the heat treatment generating the matrix are reproducibly highlighted by the DSC trace, as shown from FIG. 3d.

Evaluation of the Storage Stability

Figure 4A:
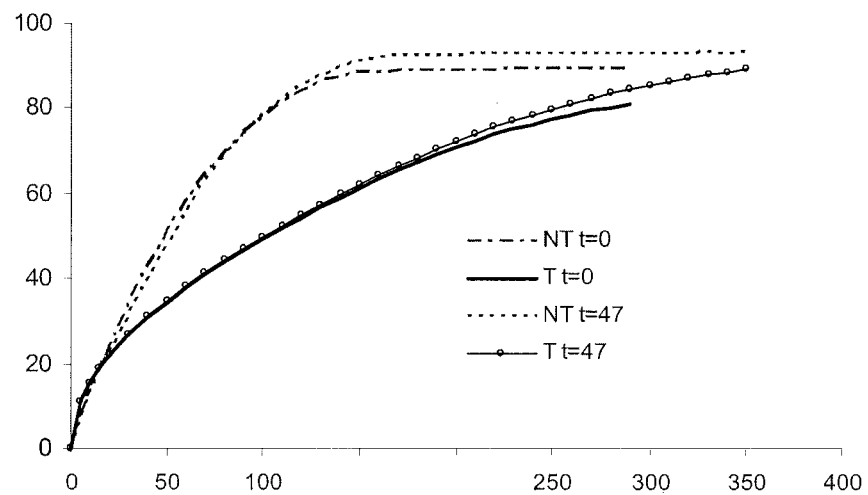
FIG. 4a shows a comparison between average dissolution profiles (n=6) in 0.05 N HCl of Diltiazem (DTZ) released from tablets according to the invention (example 1) (T) and from tablets of identical composition that are not thermally treated (NT), just produced (t=0) and after 47 days storage in blister pack.
Figure 4B:
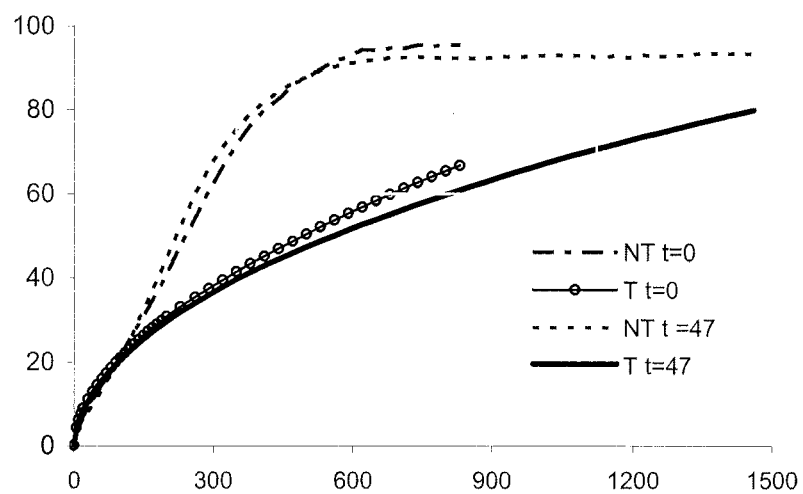
FIG. 4b shows a comparison between average dissolution profiles (n=6) in phosphate buffer (pH 72) of Diltiazem (DTZ) released from tablets according to the invention (example 1) (T) and from tablets of identical composition that are not thermally treated (NT), just produced (t=0) and after 47 days storage in blister pack.
Figure 5A:
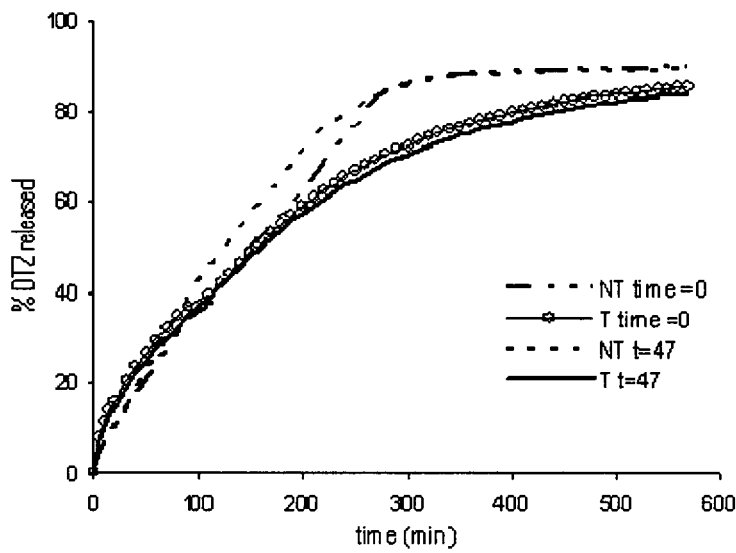
FIG. 5a shows a comparison between average dissolution profiles (n=6) in 0.05 N HCl of Diltiazem (DTZ) released from tablets according to the invention (example 2) (T) and from tablets of identical composition that are not thermally treated (NT), just produced (t=0) and after 47 days storage in blister pack.
Figure 5B:
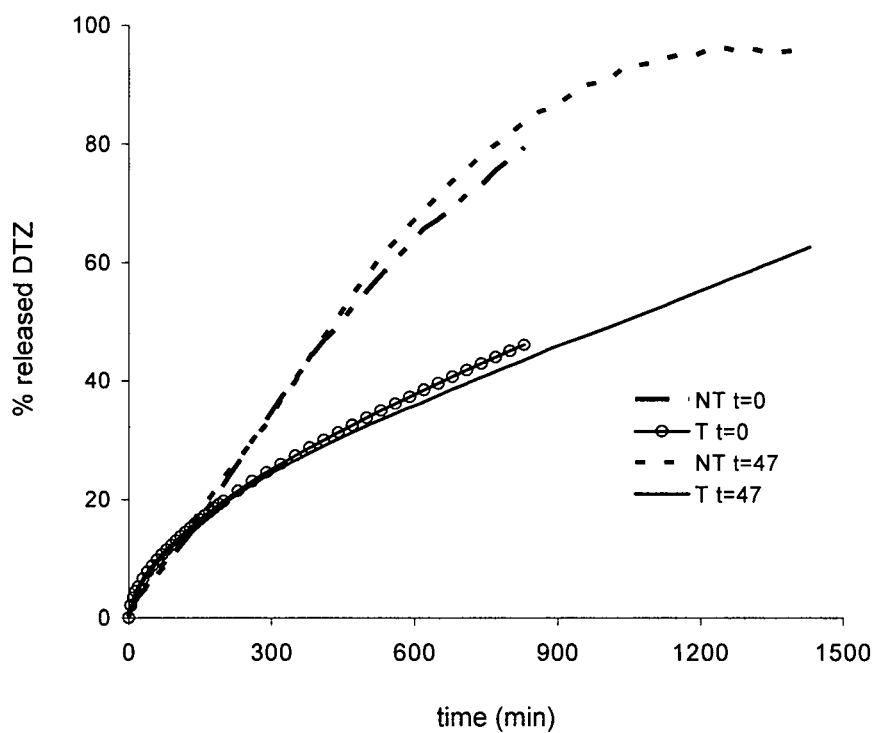
FIG. 5b shows a comparison between average dissolution profiles in phosphate buffer (pH 7.2) of Diltiazem (DTZ) released from thermally treated tablets according to the invention (example 2) (T) and from tablets of identical composition that are not thermally treated (NT), just produced (t=0) and after 47 days storage in blister pack.

The tablets obtained according to the examples 1 (FIGS. 4a and 4b) and 2 (FIGS. 5a and 5b) were studied after storage for 47 days in blister pack in order to verify if the effect of the treatment was reversible over time or not. The relevant dissolution profiles, in 0.05 N HCl (4a) and in phosphate buffer (4b), of the average of the six tablets, T and NT, were compared at t=0 and at t=47 days. In the following Table 2, several parameters are shown that were obtained from the tablets according to examples 1 and 2, stored in blister pack.

TABLE 2

| Tablets | Δw %<br>(w/w) | Water<br>content (%)<br>t = day 0 | Water<br>content (%)<br>t = day 47 | Hardness<br>N<br>t = day 0 | Hardness<br>N<br>t = day 47 |
|---|---|---|---|---|---|
| Ex. 1 NT | 0.5 | 2.57 | 3.67 | 307.8 | 285.3 |
| Ex. 1 T | 1.6 | 0.88 | 1.43 | 405.9 | 369.6 |
| Ex. 2 NT | 0.9 | 2.56 | 3.24 | 247.1 | 296.1 |
| Ex. 2 T | 1.9 | 1.26 | 2.42 | 396.1 | 397.1 |

Δw % (percentage mass increase) represents the water acquired during storage.

As seen from FIGS. 4 and 5, there are no significant differences in the release of the two tablet types after storage, even if the tablets re-acquired a certain amount of water, as shown in Table 2. In the stability study conducted for 32 months on tablets of example 2, conserved in blister pack at room temperature, the contents in water measured according to Karl Fisher are between 2.1% and 2.5%, thus in practice the restoration of the water content at the original values is confirmed over time. This leads to the idea that the prolongation of the release following heat treatment is not due to the loss of water by the matrix, but to a modification of the physical state of the components which generates such matrix, which proved to be irreversible during the storage time. Other test data, obtained after a storage time of 2-3 years, confirmed the above.

Figure 5C:
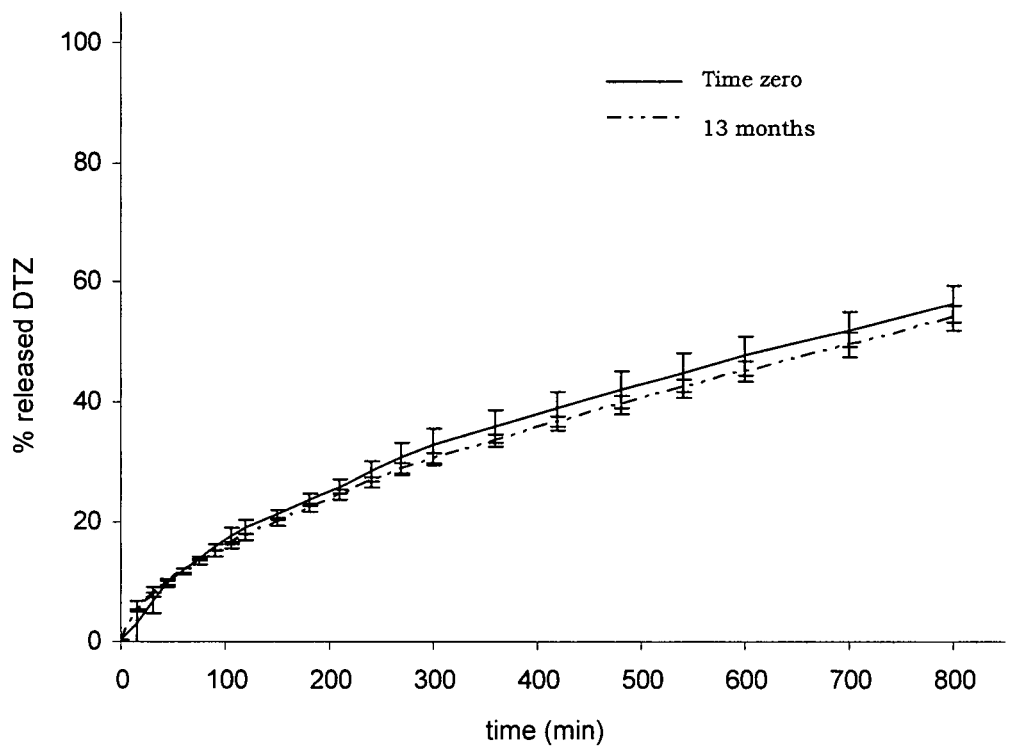
FIG. 5c shows a comparison between the average dissolution profiles in phosphate buffer (pH 7.2) of Diltiazem (DTZ) released from thermally treated tablets according to the invention (example 1) just prepared (t=0) and after a storage in blister pack of 13 months. The bars represent the 95% confidence intervals.

In FIG. 5c, the average dissolution profile is shown, in phosphate buffer, of six tablets according to example 1, just-produced and after having been stored in blister pack for 13 months at room temperature.

It is observed that the two profiles are practically superimposable.

Figure 5D:
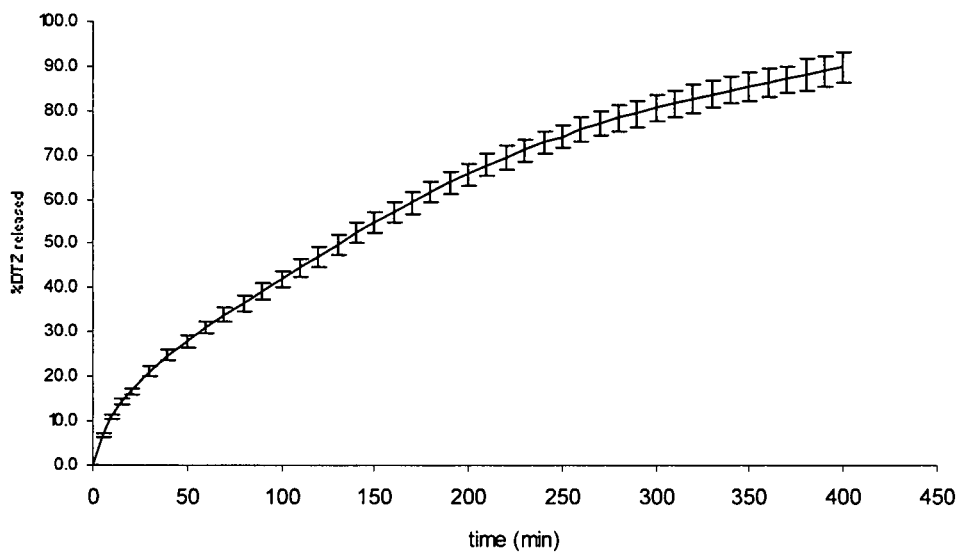
FIG. 5d presents an average dissolution profile (n=6) in 0.05 N HCl of Diltiazem (DTZ) released from tablets of a batch according to example 2, thermally treated (T), stored in blister pack for 32 months. The bars represent the 95% confidence intervals.
Figure 5E:
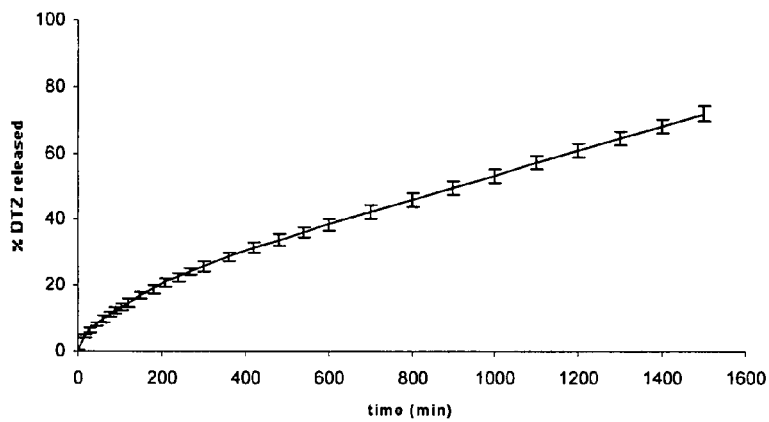
FIG. 5e presents the average dissolution profile (n=6) in phosphate buffer (pH 72) of Diltiazem (DTZ) from tablets of a batch according to example 2, thermally treated (T), stored in blister pack for 32 months. The bars represent the 95% confidence intervals.

In FIG. 5d, the average dissolution profile in 0.05 N HCl is shown of six tablets according to example 2, after 32 months storage in blister pack and in FIG. 5e the average dissolution profile is shown in phosphate buffer of six tablets according to example 2 after the same storage period.

Figure 5F:
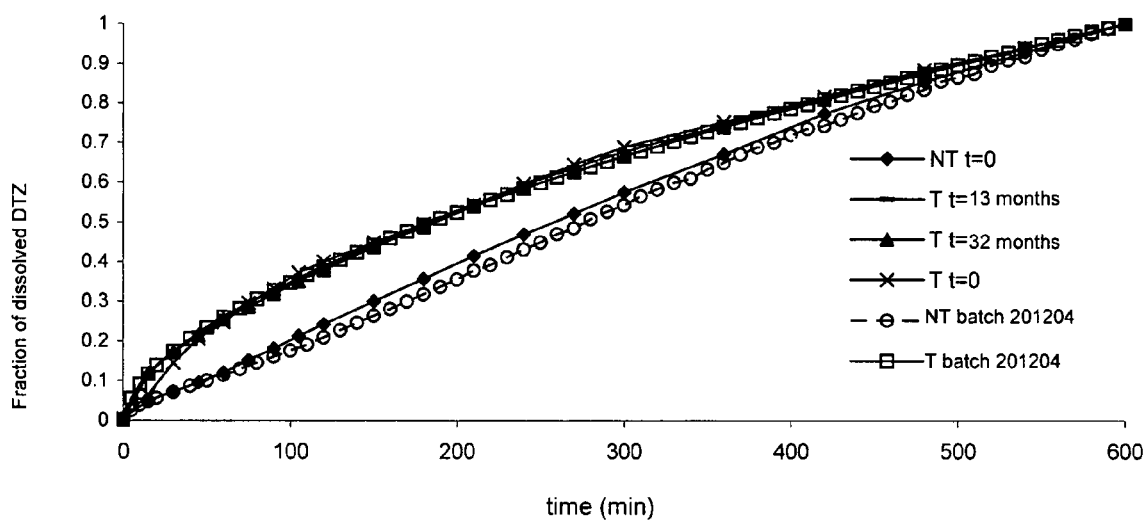
FIG. 5f shows a comparison between average profiles (n=6) of the fraction of dissolved Diltiazem (DTZ) with respect to the quantity present in solution at the time of 600 minutes in phosphate buffer (pH 7.2), of different batches of thermally treated tablets according to example 2 (T) and tablets of identical composition but not treated (NT), just produced (t=0) and stored in blister pack for 13 (t=13 months) and 32 months (t=32 months).

In FIG. 5f, the dissolution profiles are reported as dissolved DTZ fraction with respect to the dissolved quantity after 600 minutes. Such representation manner is useful for underlining the release mechanisms, while it does not give information on the release rate and on the prolongation of the active substance release. In such figure, the average dissolution profiles (n=6) in phosphate buffer are compared of different tablet batches according to example 2 and tablets of identical composition but not thermally treated (NT).

From this comparison, it is clear that the drug release mechanism from the matrices of different batches is fully superimposable and is not modified, even after storage in blister pack for 32 months. Also this representation mode underlines the different release mechanism from the compressed matrices according to the present invention compared with the non non-treated tablets. In addition, the release mechanism for the latter is less reproducible.

Comparing the results of the hardness test of Table 2 with those obtained before storage, one notes a decrease of the tensile strength of the tablets according to example 1 and its increase in the case of the tablets NT according to example 2.

In Table 3, there are reported the hardness data of tablets according to example 2, stored for 32 months.

TABLE 3

Hardness in N for tablets according to example 2, stored for 32 months.

| | Time (months) | | |
|---|---|---|---|
| | 0 | 13 | 32 |
| | 396.1 | 403.9 | 413.7 |
| | 400.0 | 403.9 | 418.6 |
| | 409.8 | 396.1 | 430.4 |
| Average | 402.0 | 401.0 | 420.6 |
| Standard deviation | 7.1 | 4.5 | 8.6 |

Thermal Process Investigations

Research was then carried out to see if the prolongation effect on the release of the active substance, obtained by means of the heat treatment of the tablets, could also be obtained by previously subjecting the excipient mixture or even single excipients to the same treatment, subsequently adding the active substance and then proceeding with the compression.

It was experimentally found that by subjecting the physical mixture of all the components according to example 2 to a heating at 150° C. for 15 minutes, or by subjecting one excipient at a time to the same heating (for example Polycarbophil, ethylcellulose or MicroceLac) before compression, tablets were obtained, after subsequent addition of the other components, which did not have the desired release profile of diltiazem. The heating of Diltiazem hydrochloride at 150° C. for 15 minutes, according to HPLC, thermoanalytical (DSC, TGA and HSM) and spectroscopic investigations, did not involve any physical or chemical modification of such active substance. Diltiazem hydrochloride so pretreated and employed for producing the tablets of example 2 did not modify the dissolution profiles from such matrices, nor did it modify the release of the tablets NT of identical composition.

From these observations, it is inferred that the heat treatment gives rise to the constitution of the matrix according to the patent application, only if carried out on a tablet in which the components, in uniform mixture with each other, are placed in close contact with each other by the thickening or plasticizing forces that are generated during the compaction or compression process.

The heat treatment modes of the tablets according to example 2 were then varied: some were treated for 15 minutes at 90° C. or at 130° C., others were treated at 150° C. for 5 minutes. The obtained dissolution profiles, compared with the curve relating to tablets treated in the manner reported in example 2, and NT tablets, are reported in FIG. 6.

Figure 6:
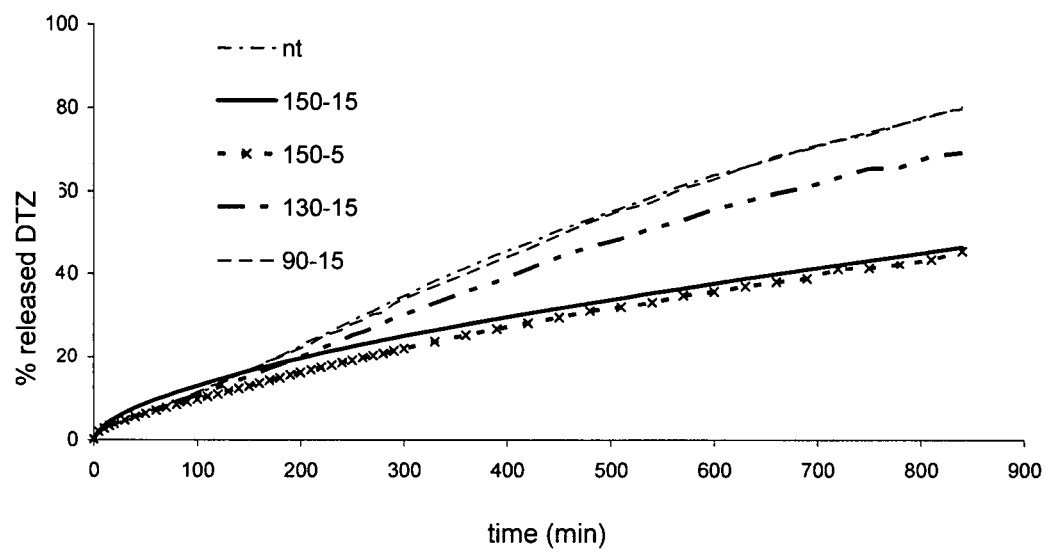
FIG. 6 shows the dissolution profiles of Diltiazem in phosphate buffer (pH 7.2) of tablets according to the present invention (example 2), subjected to different heat treatments. In particular, this figure shows a comparison of the effect of different heat treatments on the release of Diltiazem (DTZ) in phosphate buffer (pH 7.2) from tablets according to example 2. Average dissolution profiles (n=6) of tablets: nt=non-treated; 150-5=150° C.×5 min treatment; 90-15=-90° C.×15 min treatment; 150-15=150° C.×15 min treatment; 130-15=130° C.×15 min treatment.

It is noted from FIG. 6 that all the tablets show zero order release kinetics, even if the tablets treated at 150° C. for 5 or 15 minutes have an accentuated prolongation of the active substance release with respect to those treated at 130° C. The latter tablets in any case show a release prolongation of the active substance with respect to the NT tablets and an appreciable swelling degree after the dissolution test, even if both are of lesser extent than those seen with the tablets treated at 150° C.

This data matches the observation that, after the dissolution test in phosphate buffer, in the tablets treated at 130° for 15 minutes, the swelling is minimal and the gelatinous layer hard to appreciate, and in those treated at 90°, but for only 15 minutes, no visual modification is observed with respect to the NTs.

This data indicates that the active substance release rate can also be modulated through the choice of suitable heat treatment temperature and time parameters.

Adhesion Tests

Tablets were then prepared without DTZ, containing the three excipients of example 2 in the same reciprocal weight ratios: an adhesion test was conducted on these tablets and on the tablets according to example 2 according to above-reported procedure, carried out by means of a tensiometer. The Tables 3bis and 4 show the water content of the tablets analyzed and the results obtained from such test.

As can be seen from the data presented in Table 4, the NT tablets without DTZ show a certain adhesion to the substrate (mucin) which simulates the gastro-intestinal mucosa, which decreases following treatment, a phenomenon which is probably correlated to the structural modifications of the matrices produced by the heat treatment.

Figure 7:
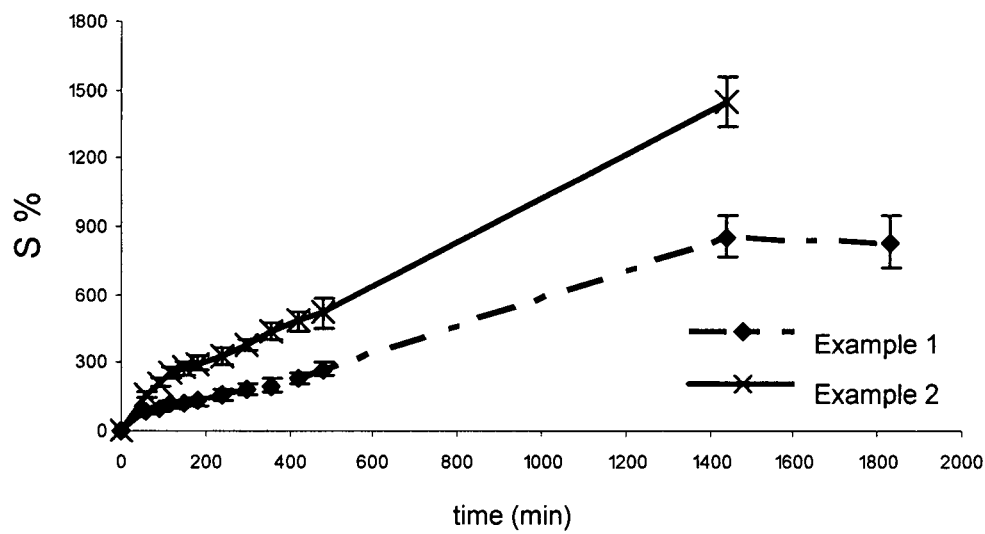
FIG. 7 graphically shows the swelling percentage level (S %) of tablets according to the present invention. In particular, it shows a comparison between average swelling profiles (n=3) of the thermally treated tablets according to examples 1 and 2. The bars represent the standard deviation values.

Regarding the NTs, the tablets containing the drug show less adhesion than those formulated with only the excipients. This could be due to the different composition; in fact, even if the ratios between the components are kept constant, the tablets without DTZ contain an absolute quantity of Polycarbophil which is greater by 25% with respect to example 2. The results obtained from the treated tablets show a decrease of the adhesion in the case of treatment at 130° C. with respect to the NTs containing the drug, while after the treatment at 150° C.×15 minutes, the adhesive properties did not diminish, Swelling Tests The swelling process was studied on the tablets obtained according to example 1 and 2, at 37 .degree. C. in phosphate buffer at pH 7.2, pH conditions in which the phenomenon is particularly evident. FIG. 7 shows the percentage swelling degree (S %) of the two tablet types according to examples 1 and 2. The obtained curves describe the average swelling of three tablets per type, the bars indicate the standard deviation.

In Table 5, the following are reported: $S\%_{60}$, $S\%_{max}$, the weight and the volume of the tablets after 24 ore of immersion in phosphate buffer and the relevant densities.

TABLE 3bis

| Tablets | Composition | Water content (%) |
|---|---|---|
| NT (without Diltiazem) | 37.5% ML, 37.5% EC, 25% POL | 3.84 |
| T (without Diltiazem) | | 0.68 |
| NT | 20% DTZ, 30% ML, 30% EC, 20% POL | 2.77 |
| T (150° C. × 15 min) | | 0.53 |
| T' (130° C. × 15 min) | | 1.57 |

NT = untreated;
T = treated at 150° C. for 5 minutes;
T' = treated at 130° C. for 15 minutes.
DTZ = Diltiazem;
ML = MicroceLac;
EC = ethylcellulose;
POL = Polycarbophil.

TABLE 5

| Parameters | Tablets T, example 1 | Tablets T, example 2 |
|---|---|---|
| $S\%_{60}$ | 82.8 | 161.0 |
| $S\%_{max}$ | 832.9 | 1450.0 |
| Tmax (hours) | 24 | 24 |
| Weight (mg) | 1546.5 | 2669.7 |
| Volume (mL) | 1.30 | 2.60 |
| Density (g/mL) | 1.19 | 1.03 |

Table 5: several parameters evaluated on tablets treated according to examples 1 and 2; the values represent the average of three tablets per type.
$S\%_{60}$ represents the swelling degree after the first measurement (60 minutes),
$S\%_{max}$ represents the maximum swelling level obtained,
Tmax the time at which the maximum swelling is achieved.

As seen in FIG. 7, the tablets treated according to example 2 have a swelling degree and rate that is higher with respect to the tablets treated according to claim 1, as also shown in Table 5: this property seems to be correlated to the concentration of the Polycarbophil in the mixture. It should be noted that for both there is a mass increase, on the basis of which S is calculated, that is constant over time except for the first 120 minutes.

TABLE 4

| Tablets | Maximum load (N) | Standard deviation (N) | Work (N × mm) | Standard deviation (N × mm) | Unit load (MPa) | Standard deviation (MPa) |
|---|---|---|---|---|---|---|
| NT (without DTZ) | 6.96 | 0.19 | 0.84 | 0.20 | 0.052 | 0.002 |
| T (without DTZ) | 4.30 | 0.24 | 0.63 | 0.11 | 0.032 | 0.002 |
| NT | 4.41 | 0.36 | 0.57 | 0.08 | 0.033 | 0.002 |
| T (150° C. × 15 min) | 4.87 | 0.81 | 0.83 | 0.19 | 0.037 | 0.007 |
| T' (130° C. × 15 min) | 2.94 | 1.03 | 0.38 | 0.15 | 0.022 | 0.008 |

NT = untreated;
T = treated at 150° C. for 5 minutes;
T' = treated at 130° C. for 15 minutes.
Table 4: data obtained from the adhesion tests carried out on the tablets without DTZ and on the tablets according to example 2 and related standard deviations. The reported results represent the average values of three measurements for each tablet type.

The tablets according to example 1 reach a maximum time of 1440 minutes (24 hours) beyond which they do not further swell but remain immersed without disintegration for up to 1830 minutes (30.5 hours), while for the tablets according to example 2 this phenomenon is not visualized, since after having reached the maximum at 24 hours (time at which the last measurement was made) the tablets tend to completely disintegrate between 24 and 30 hours. These phenomena are observed at the in vitro measurement conditions, which involve a high volume of aqueous medium and continuous stirring.

Figure 7A:
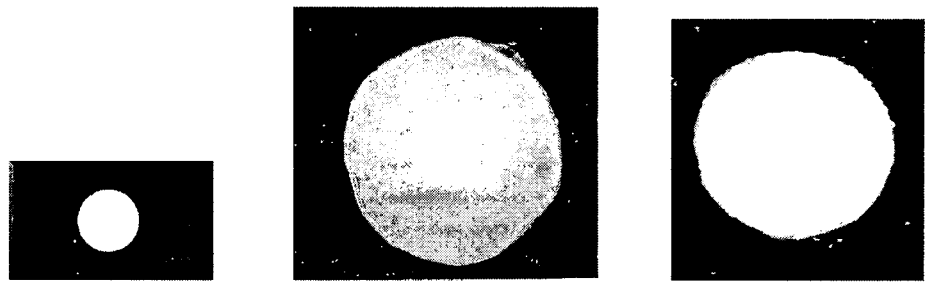
In FIG. 7a, three photographs are reported illustrating thermally treated tablets according to the present invention before the dissolution test and at the end of the dissolution test in phosphate buffer, when these have reached the maximum swelling degree. From left to right, the following photographs are reported: original-size tablet of examples 1 or 2 before the dissolution test; tablet according to example 2 at the maximum swelling degree reached at the end of the dissolution test at 37° C. in phosphate buffer; tablet according to example 1 at the maximum swelling degree reached at the end of the dissolution test at 37° C. in phosphate buffer.

In FIG. 7, the swelling profiles are reported of the tablets according to examples 1 and 2 in phosphate buffer at 37° C. In FIG. 7a, there are the photographs of the tablets, according to the two examples, taken at their maximum swelling degree, compared with the photograph of the tablet in its original size before the dissolution test.

Figure 7B:
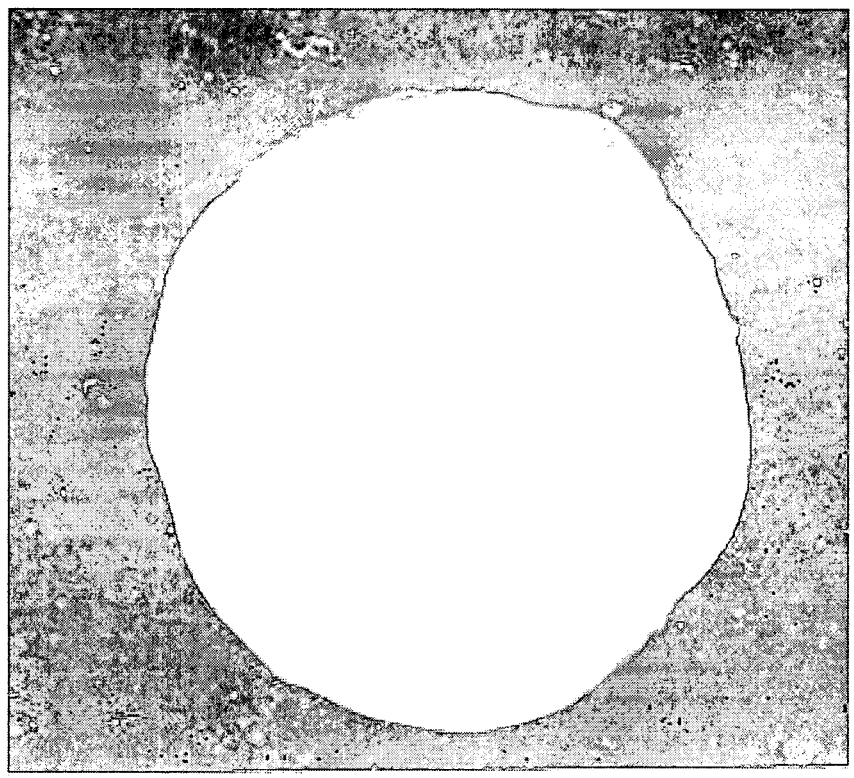
FIG. 7b is an enlarged photograph of a thermally treated tablet according to the present invention, at the maximum swelling degree reached at the end of the dissolution test. In particular, it is an enlargement of the photograph reported in FIG. 7a at the centre: tablet according to example 2 at the maximum swelling degree reached at the end of the dissolution test at 37° C. in phosphate buffer.

In FIG. 7b, the enlargement of the tablet according to example 2 is reported at its maximum swelling degree, where the solid central core is clearly seen.

Figure 7C:
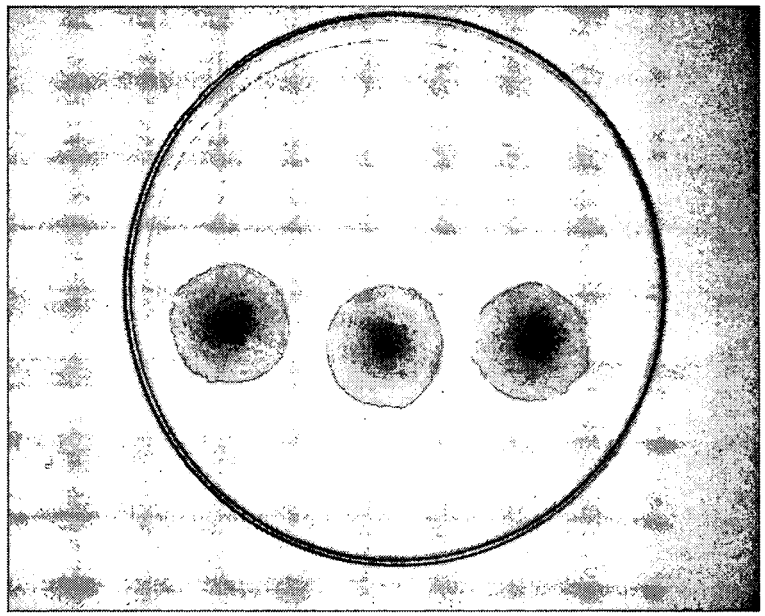
In FIG. 7c, the following two photographs are reported: above, a photograph of three tablets according to the invention at the maximum swelling degree, below a perspective view of a tablet according to the invention at the maximum swelling degree. In particular there are shown photographs of thermally treated tablets according to example 2 at the maximum swelling degree reached at the end of the dissolution test at 37° C. in phosphate buffer (pH=7.2).
Figure 7C:
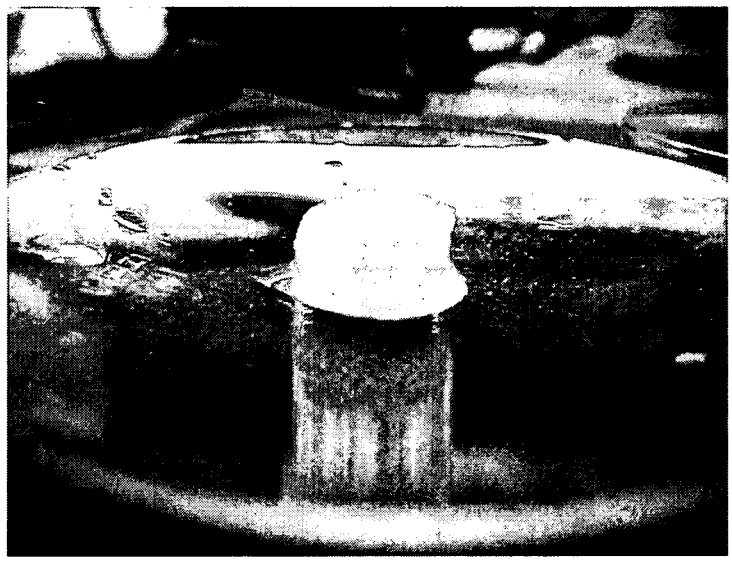

In FIG. 7C, there are the photographs of swollen tablets according to example 2, from different perspectives where the formation of a consistent matrix is clearly seen.

Figure 7D:
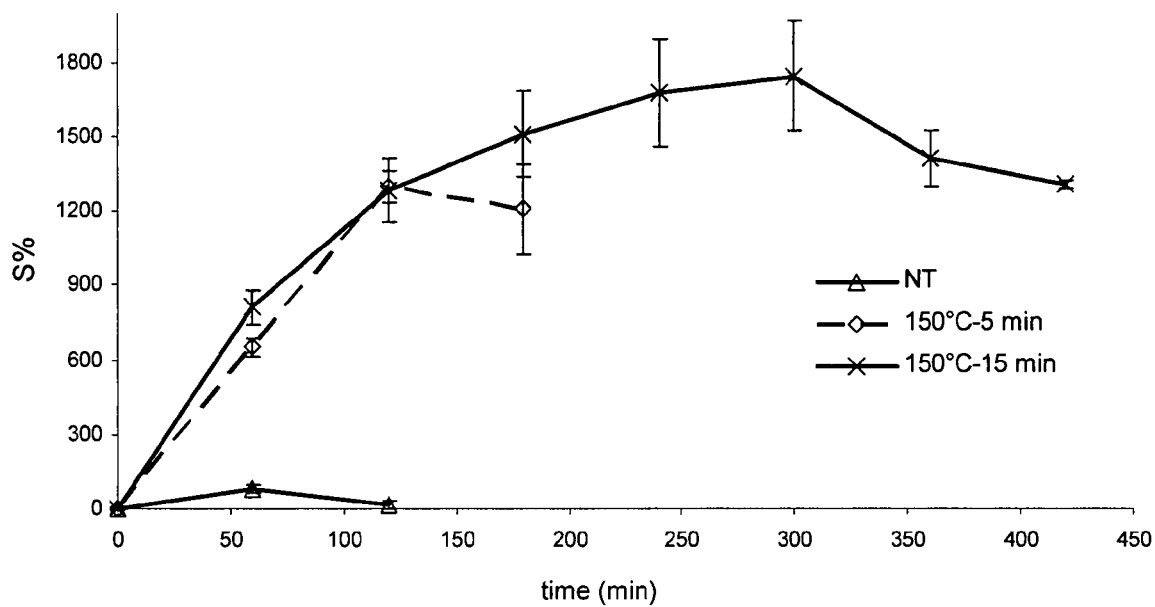
FIG. 7d reports a graph which illustrates the swelling of compressed matrices without active substance according to the invention. This graph shows, in particular, a comparison between the average swelling profiles (n=3) of matrices without active substance and with ratios between the components according to example 2, obtained with two different heat treatments (5 or 15 min. at 150° C.) or not subjected to heat treatment (NT).

The swelling was also measured on matrices without active substance. In FIG. 7d, the swelling profiles are reported of tablets containing all the components of example 2 except DTZ but in the same ratios as the example. The greatest swelling is achieved by the matrices produced with the longest heat treatment, 150° C. for 15 minutes: these attain the maximum weight increase value, equal to 1744%, after 5 hours, and resist erosion, produced by the continuous stirring, for another two hours.

The matrices produced with the 5 minutes heating reach the maximum weight increase value (1282%) after two hours and resist erosion for another 60 minutes.

The presence of the drug in the matrices obtained through heating slows the swelling phenomenon due to the diffusion of the aqueous medium in the swelling matrix. The slowing is correlated to the reverse mass process, i.e. the outward diffusion of the active substance. The simultaneousness of the two phenomena could explain the active substance release kinetics according to the zero order model.

The effect of the heat treatment on the matrix formation is also clear from the behaviour of the NT tablets, registered during the swelling study. Indeed, these swell very little, only 80%, in the first hour and then completely disintegrate after 120 minutes.

Example 4

| | |
|---|---|
| Gliclazide | 20% |
| Ethylcellulose | 30% |
| MicroceLac | 30% |
| Polycarbophil | 20% |

From this powder mixture, tablets were prepared by direct compression according to the above-illustrated procedure.

A part of these tablets was subjected to a heat treatment in the above-illustrated way, maintaining them at the treatment temperature of 150° C. for a time of 5 or 15 minutes. After such time had passed, the oven was immediately cooled to room temperature by means of forced ventilation. Minimum conditioning time at room temperature before packaging: 5 minutes.

Figure 8:
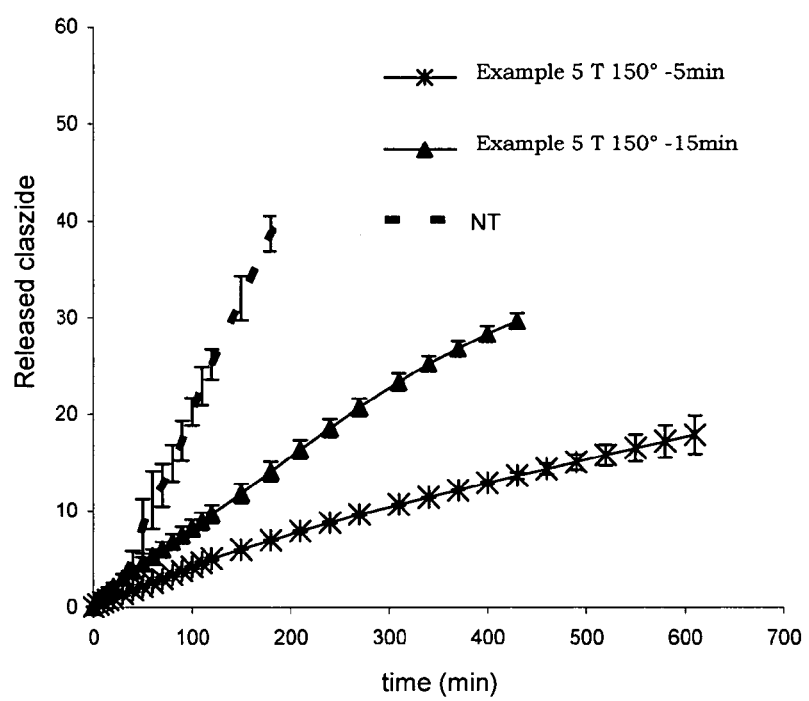
FIG. 8 shows the average dissolution profiles (n=6) in phosphate buffer (pH 7.2) of Gliclazide released from tablets (T) obtained with the method of the present invention (example 4) (thermally treated at 150° C. for 5 and 15 minutes) compared with tablets of identical composition but not subjected to heat treatment (NT). The bars represent 95% confidence intervals.

In FIG. 8, the average dissolution profile is reported of six tablets for every treatment type (150° C. for 15 minutes and 150° C. for 5 minutes) compared with the average dissolution profile of the NTs in phosphate buffer at pH 7.2.

The effect of the heat treatment on the formation of the matrix is clear from the control on the Gliclazide release rate and visually from the swelling of the units for the formation of a compact gel crown.

It is clear that the effect of the heat treatment also varies as a function of the type of active substance, due to the different interactions with the matrix components.

The invention claimed is:

1. A method for the preparation of a bioadhesive compact matrix, which comprises the steps of:
    preparing a uniform mixture of powders comprising at least one alkylcellulose or one hydroxyalkylcellulose and a, non-water-soluble, water-swellable cross-linked polycarboxylic polymer;
    preparing compressed or compact units starting from said powder mixture by direct compression; and
    subjecting the compressed or compact units thus obtained to heating at a temperature in the range of 130-160° C. for a time of 1-30 minutes.

2. The method according to claim 1, for the preparation of bioadhesive compressed units, containing at least one active substance and adapted for a prolonged or controlled release of said at least one active substance, wherein said uniform powder mixture also comprises at least one active substance.

3. The method according to claim 1, wherein said uniform powder mixture further comprises a diluent, selected from the group consisting of anhydrous or monohydrate lactose, in any amorphous or crystalline physical form, and microcrystalline cellulose or mixtures thereof.

4. The method according to claim 1, wherein said alkylcellulose is selected from the group consisting of methylcellulose and ethylcellulose, and said hydroxyalkylcellulose is selected from the group consisting of hydroxypropylcellulose, hydroxypropylmethylcellulose, hydroxyethylcellulose and hydroxyethylmethylcellulose.

5. The method according to claim 1 wherein said non-water-soluble, water-swellable cross-linked polycarboxylic polymer is Polycarbophil.

6. The method according to claim 1, wherein said uniform powder mixture further comprises one or more components selected from the group consisting of Crospovidone, Povidone, Vinylpyrrolidone-vinyl acetate copolymer, Cellulose acetate phthalate, Hypromellose phthalate, Polyvinyl alcohol, Polyvinyl acetate phthalate, Cyclodextrin, methacrylate polymers, glyceryl triacetate, triethyl citrate, tributyl citrate, acetyl triethyl citrate, acetyl tributyl citrate, dibutyl sebacate, diethyl phthalate, dibutyl phthalate, dioctyl phosphate, polyethylene glycol, Polyethylene oxides, calcium carboxymethylcellulose, sodium carboxymethylcellulose, Inuline, Chitosan, Guar gum, Xanthan gum, Tragacanth gum, Carbomer, Carrageenan, Alginic acid, Poloxamer, Aliphatic polyesters, Cellulose acetate butyrate, Chitosan lactate, Pectin, Polyethylene-co-vinyl acetate, Polyethylene, polyvinyl acetate-co-methacrylic acid, Carnauba wax, butylated hydroxyanisole, butylated hydroxytoluene, ascorbyl palmitate, glyceryl palmitostearate, hydrogenated soybean and castor oil, Glyceryl monostearate, d-a-tocopherol (Vitamin E), Vitamin E Succinate, Vitamin E and TPGS, Methyl Paraben, butyl stearate, stearyl alcohol, saccharose monopalmitate (Sucroester), Glycerol esters and PEG esters, polyoxyethylene alkyl ethers, Glyceryl palmitostearate, mineral oil and castor oil.

7. The method according to claim 1, wherein said uniform powder mixture comprises at least one active substance, a spray-dried compound containing 75% alpha-lactose monohydrate and 25% microcrystalline cellulose, ethylcellulose and Polycarbophil.

8. The method according to claim 7, wherein Polycarbophil constitutes 5-35% by weight of the total weight of said powder mixture.

9. The method according to claim 8, wherein ethylcellulose and the spray-dried compound containing 75% alpha-lactose monohydrate and 25% microcrystalline cellulose are present in said powder mixture in a weight ratio that varies from 1:2 to 2:1 together constitute 45-95% by weight of the total weight of said powder mixture, and ethylcellulose is present in a weight ratio with the Polycarbophil that varies from 1:5 to 5:1.

10. The method according to claim 8, wherein said at least one active substance is contained in said powder mixture in a quantity that comprises at least 0.001 ppm of the mixture.

11. The method according to claim 1, wherein said compressed unit is a pharmaceutical tablet and said active substance is a pharmacologically active substance.

12. The method according to claim 3, wherein said uniform powder mixture comprises a spray-dried compound containing 75% alpha-lactose monohydrate and 25% microcrystalline cellulose.

13. The method according to claim 8, wherein Polycarbophil constitutes 10-25% by weight of the total weight of said powder mixture.

14. The method according to claim 9, wherein ethylcellulose and the spray-dried compound containing 75% alpha-lactose monohydrate and 25% microcrystalline cellulose are present in said powder mixture in a weight ratio that varies from 0.8:1 to 1.2:1.

15. The method according to claim 9, wherein ethylcellulose and the spray-dried compound containing 75% alpha-lactose monohydrate and 25% microcrystalline cellulose together constitute 60-80%, by weight of the total weight of said powder mixture.

16. The method according to claim 8, wherein said at least one active substance is contained in said powder mixture in a quantity of up to 50% by weight of the total weight of the mixture.

\* \* \* \* \*